US011759264B2

(12) United States Patent
Koyrakh et al.

(10) Patent No.: US 11,759,264 B2
(45) Date of Patent: *Sep. 19, 2023

(54) SYSTEM AND METHOD FOR IDENTIFYING A LOCATION AND/OR AN ORIENTATION OF AN ELECTROMAGNETIC SENSOR BASED ON A MAP

(71) Applicant: Covidien LP, Mansfield, MA (US)

(72) Inventors: Lev A. Koyrakh, Plymouth, MN (US);
Sean M. Morgan, Minneapolis, MN (US)

(73) Assignee: COVIDIEN LP, Mansfield, MA (US)

( * ) Notice: Subject to any disclaimer, the term of this patent is extended or adjusted under 35 U.S.C. 154(b) by 335 days.

This patent is subject to a terminal disclaimer.

(21) Appl. No.: 16/922,198

(22) Filed: Jul. 7, 2020

(65) Prior Publication Data
US 2020/0330165 A1    Oct. 22, 2020

Related U.S. Application Data

(63) Continuation of application No. 15/337,166, filed on Oct. 28, 2016, now Pat. No. 10,722,311.

(51) Int. Cl.
*A61B 34/20* (2016.01)
*A61B 34/10* (2016.01)

(52) U.S. Cl.
CPC .............. *A61B 34/20* (2016.02); *A61B 34/10* (2016.02); *A61B 2034/107* (2016.02); *A61B 2034/2051* (2016.02); *A61B 2034/2053* (2016.02)

(58) Field of Classification Search
CPC ...... A61B 2034/107; A61B 2034/2051; A61B 2034/2053; A61B 34/10; A61B 34/20
See application file for complete search history.

(56) References Cited

U.S. PATENT DOCUMENTS 1,576,781 A    3/1926  Phillips
1,735,726 A    11/1929 Bornhardt
(Continued)

FOREIGN PATENT DOCUMENTS

CA          964149    3/1975
CN       101820810 A  9/2010
(Continued)

OTHER PUBLICATIONS

International Search Report and Written Opinion dated Feb. 8, 2018 and issued in corresponding International Application No. PCT/US2017/058421. cited byapplicant.

(Continued)

*Primary Examiner* — Michael T Rozanski
(74) *Attorney, Agent, or Firm* — WEBER ROSSELLI & CANNON LLP

(57) ABSTRACT

Systems and methods for identifying a location and/or an orientation of an electromagnetic (EM) sensor navigated within an EM volume are provided. Calculated EM field strengths at each gridpoint of a second set of gridpoints of the EM volume are retrieved from a memory. An EM field is generated by way of an antenna assembly. A measured EM field strength is received from the EM sensor. A first gridpoint among a first set of gridpoints of the EM volume is identified based on the measured EM field strength and a high density (HD) map. The location and/or the orientation of the EM sensor is identified based on the HD map, using the first gridpoint as an initial condition, with the second set of gridpoints also including the first set of gridpoints.

20 Claims, 5 Drawing Sheets

(56) References Cited

U.S. PATENT DOCUMENTS

| | | |
|---|---|---|
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,121,228 A | 2/1964 | Kalmus |
| 3,294,083 A | 12/1966 | Alderson |
| 3,367,326 A | 2/1968 | Frazier |
| 3,439,256 A | 4/1969 | Kahne et al. |
| 3,519,436 A | 7/1970 | Bauer et al. |
| 3,577,160 A | 5/1971 | White |
| 3,600,625 A | 8/1971 | Tsuneta et al. |
| 3,605,725 A | 9/1971 | Bentov |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,822,697 A | 7/1974 | Komiya |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,135,184 A | 1/1979 | Pruzick |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,249,167 A | 2/1981 | Purinton et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,308,530 A | 12/1981 | Kip et al. |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,341,385 A | 7/1982 | Doyle et al. |
| 4,346,384 A | 8/1982 | Raab |
| 4,358,856 A | 11/1982 | Stivender et al. |
| 4,368,536 A | 1/1983 | Pfeiler |
| 4,394,831 A | 7/1983 | Egli et al. |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,425,511 A | 1/1984 | Brosh |
| 4,431,005 A | 2/1984 | McCormick |
| 4,447,224 A | 5/1984 | DeCant, Jr. et al. |
| 4,447,462 A | 5/1984 | Tafur et al. |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,586,491 A | 5/1986 | Carpenter |
| 4,587,975 A | 5/1986 | Salo et al. |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,686,695 A | 8/1987 | Macovski |
| 4,688,037 A | 8/1987 | Krieg |
| 4,696,544 A | 9/1987 | Costella |
| 4,697,595 A | 10/1987 | Breyer et al. |
| 4,701,049 A | 10/1987 | Beckman et al. |
| 4,704,602 A | 11/1987 | Asbrink |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,726,355 A | 2/1988 | Okada |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,784,117 A | 11/1988 | Miyazaki |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,250 A | 5/1989 | Rotier |
| 4,829,373 A | 5/1989 | Lebed et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |

(56) References Cited

U.S. PATENT DOCUMENTS

| | | |
|---|---|---|
| 4,923,459 A | 5/1990 | Nambu |
| 4,931,056 A | 6/1990 | Ghajar et al. |
| 4,945,305 A | 7/1990 | Blood |
| 4,945,912 A | 8/1990 | Langberg |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,047 A | 5/1991 | Schwab |
| 5,013,317 A | 5/1991 | Cole et al. |
| 5,016,639 A | 5/1991 | Allen |
| 5,017,139 A | 5/1991 | Mushabac |
| 5,023,102 A | 6/1991 | Given, Jr. |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| RE33,662 E | 8/1991 | Blair et al. |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,070,462 A | 12/1991 | Chau |
| 5,078,140 A | 1/1992 | Kwoh |
| 5,079,699 A | 1/1992 | Tuy et al. |
| 5,082,286 A | 1/1992 | Ryan et al. |
| 5,086,401 A | 2/1992 | Glassman et al. |
| 5,088,928 A | 2/1992 | Chan |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,104,393 A | 4/1992 | Isner et al. |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,127,408 A | 7/1992 | Parsons et al. |
| 5,129,654 A | 7/1992 | Bogner |
| 5,142,930 A | 9/1992 | Allen et al. |
| 5,143,076 A | 9/1992 | Hardy et al. |
| 5,152,277 A | 10/1992 | Honda et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,130 A | 1/1993 | Kaiya |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,188,368 A | 2/1993 | Ryan |
| 5,190,059 A | 3/1993 | Fabian et al. |
| 5,190,285 A | 3/1993 | Levy et al. |
| 5,193,106 A | 3/1993 | DeSena |
| 5,196,928 A | 3/1993 | Karasawa et al. |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,203,337 A | 4/1993 | Feldman |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,262,722 A | 11/1993 | Hedengren et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,301,061 A | 4/1994 | Nakada et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,307,816 A | 5/1994 | Hashimoto et al. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,327,889 A | 7/1994 | Imran |
| 5,329,944 A | 7/1994 | Fabian et al. |
| 5,330,485 A | 7/1994 | Clayman et al. |
| 5,333,168 A | 7/1994 | Fernandes et al. |
| 5,341,807 A | 8/1994 | Nardella |
| 5,347,289 A | 9/1994 | Elhardt |
| 5,353,795 A | 10/1994 | Souza et al. |
| 5,353,800 A | 10/1994 | Pohndorf et al. |
| 5,353,807 A | 10/1994 | DeMarco |
| 5,357,253 A | 10/1994 | Van Etten et al. |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,376,795 A | 12/1994 | Hasegawa et al. |
| 5,377,678 A | 1/1995 | Dumoulin et al. |
| 5,383,454 A | 1/1995 | Bucholz |
| 5,383,852 A | 1/1995 | Stevens-Wright |
| 5,385,146 A | 1/1995 | Goldreyer |
| 5,385,148 A | 1/1995 | Lesh et al. |
| 5,386,828 A | 2/1995 | Owens et al. |
| 5,389,073 A | 2/1995 | Imran |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,321 A | 3/1995 | Houser et al. |
| 5,397,329 A | 3/1995 | Allen |
| 5,398,684 A | 3/1995 | Hardy |
| 5,398,691 A | 3/1995 | Martin et al. |
| 5,399,146 A | 3/1995 | Nowacki et al. |

(56) References Cited

U.S. PATENT DOCUMENTS

| | | | |
|---|---|---|---|
| 5,400,384 | A | 3/1995 | Fernandes et al. |
| 5,400,771 | A | 3/1995 | Pirak et al. |
| 5,402,801 | A | 4/1995 | Taylor |
| 5,405,346 | A | 4/1995 | Grundy et al. |
| 5,408,409 | A | 4/1995 | Glassman et al. |
| 5,409,000 | A | 4/1995 | Imran |
| 5,412,414 | A | 5/1995 | Ast et al. |
| 5,413,573 | A | 5/1995 | Koivukangas |
| 5,417,210 | A | 5/1995 | Funda et al. |
| 5,419,325 | A | 5/1995 | Dumoulin et al. |
| 5,423,334 | A | 6/1995 | Jordan |
| 5,425,367 | A | 6/1995 | Shapiro et al. |
| 5,425,382 | A | 6/1995 | Golden et al. |
| 5,426,683 | A | 6/1995 | O'Farrell, Jr. et al. |
| 5,426,687 | A | 6/1995 | Goodall et al. |
| 5,427,097 | A | 6/1995 | Depp |
| 5,429,132 | A | 7/1995 | Guy et al. |
| 5,433,198 | A | 7/1995 | Desai |
| 5,435,573 | A | 7/1995 | Oakford |
| RE35,025 | E | 8/1995 | Anderton |
| 5,437,277 | A | 8/1995 | Dumoulin et al. |
| 5,443,066 | A | 8/1995 | Dumoulin et al. |
| 5,443,489 | A | 8/1995 | Ben-Haim |
| 5,444,756 | A | 8/1995 | Pai et al. |
| 5,445,144 | A | 8/1995 | Wodicka et al. |
| 5,445,150 | A | 8/1995 | Dumoulin et al. |
| 5,445,166 | A | 8/1995 | Taylor |
| 5,446,548 | A | 8/1995 | Gerig et al. |
| 5,447,154 | A | 9/1995 | Cinquin et al. |
| 5,447,156 | A | 9/1995 | Dumoulin et al. |
| 5,448,610 | A | 9/1995 | Yamamoto et al. |
| 5,453,686 | A | 9/1995 | Anderson |
| 5,456,254 | A | 10/1995 | Pietroski et al. |
| 5,456,664 | A | 10/1995 | Heinzelman et al. |
| 5,456,689 | A | 10/1995 | Kresch et al. |
| 5,456,718 | A | 10/1995 | Szymaitis |
| 5,457,641 | A | 10/1995 | Zimmer et al. |
| 5,458,718 | A | 10/1995 | Venkitachalam |
| 5,464,446 | A | 11/1995 | Dreessen et al. |
| 5,469,847 | A | 11/1995 | Zinreich et al. |
| 5,472,441 | A | 12/1995 | Edwards et al. |
| 5,476,100 | A | 12/1995 | Galel |
| 5,476,495 | A | 12/1995 | Kordis et al. |
| 5,478,341 | A | 12/1995 | Cook et al. |
| 5,478,343 | A | 12/1995 | Ritter |
| 5,480,422 | A | 1/1996 | Ben-Haim |
| 5,480,439 | A | 1/1996 | Bisek et al. |
| 5,483,961 | A | 1/1996 | Kelly et al. |
| 5,485,849 | A | 1/1996 | Panescu et al. |
| 5,487,391 | A | 1/1996 | Panescu |
| 5,487,729 | A | 1/1996 | Avellanet et al. |
| 5,487,757 | A | 1/1996 | Truckai et al. |
| 5,489,256 | A | 2/1996 | Adair |
| 5,490,196 | A | 2/1996 | Rudich et al. |
| 5,492,131 | A | 2/1996 | Galel |
| 5,492,713 | A | 2/1996 | Sommermeyer |
| 5,493,517 | A | 2/1996 | Frazier |
| 5,494,034 | A | 2/1996 | Schlondorff et al. |
| 5,503,416 | A | 4/1996 | Aoki et al. |
| 5,513,637 | A | 5/1996 | Twiss et al. |
| 5,514,146 | A | 5/1996 | Lam et al. |
| 5,515,160 | A | 5/1996 | Schulz et al. |
| 5,515,853 | A | 5/1996 | Smith et al. |
| 5,517,990 | A | 5/1996 | Kalfas et al. |
| 5,520,059 | A | 5/1996 | Garshelis |
| 5,522,814 | A | 6/1996 | Bernaz |
| 5,522,815 | A | 6/1996 | Durgin, Jr. et al. |
| 5,531,227 | A | 7/1996 | Schneider |
| 5,531,520 | A | 7/1996 | Grimson et al. |
| 5,531,686 | A | 7/1996 | Lundquist et al. |
| 5,542,938 | A | 8/1996 | Avellanet et al. |
| 5,543,951 | A | 8/1996 | Moehrmann |
| 5,545,200 | A | 8/1996 | West et al. |
| 5,546,940 | A | 8/1996 | Panescu et al. |
| 5,546,949 | A | 8/1996 | Frazin et al. |
| 5,546,951 | A | 8/1996 | Ben-Haim |
| 5,551,429 | A | 9/1996 | Fitzpatrick et al. |
| 5,555,883 | A | 9/1996 | Avitall |
| 5,558,091 | A | 9/1996 | Acker et al. |
| 5,566,681 | A | 10/1996 | Manwaring et al. |
| 5,568,384 | A | 10/1996 | Robb et al. |
| 5,568,809 | A | 10/1996 | Ben-haim |
| 5,571,083 | A | 11/1996 | Lemelson |
| 5,572,999 | A | 11/1996 | Funda et al. |
| 5,573,533 | A | 11/1996 | Strul |
| 5,575,794 | A | 11/1996 | Walus et al. |
| 5,575,798 | A | 11/1996 | Koutrouvelis |
| 5,577,991 | A | 11/1996 | Akui et al. |
| 5,583,909 | A | 12/1996 | Hanover |
| 5,588,033 | A | 12/1996 | Yeung |
| 5,588,430 | A | 12/1996 | Bova et al. |
| 5,590,215 | A | 12/1996 | Allen |
| 5,592,939 | A | 1/1997 | Martinelli |
| 5,595,193 | A | 1/1997 | Walus et al. |
| 5,596,228 | A | 1/1997 | Anderton et al. |
| 5,599,305 | A | 2/1997 | Hermann et al. |
| 5,600,330 | A | 2/1997 | Blood |
| 5,603,318 | A | 2/1997 | Heilbrun et al. |
| 5,606,975 | A | 3/1997 | Liang et al. |
| 5,611,025 | A | 3/1997 | Lorensen et al. |
| 5,617,462 | A | 4/1997 | Spratt |
| 5,617,857 | A | 4/1997 | Chader et al. |
| 5,619,261 | A | 4/1997 | Anderton |
| 5,620,734 | A | 4/1997 | Wesdorp et al. |
| 5,622,169 | A | 4/1997 | Golden et al. |
| 5,622,170 | A | 4/1997 | Schulz |
| 5,627,873 | A | 5/1997 | Hanover et al. |
| 5,628,315 | A | 5/1997 | Vilsmeier et al. |
| 5,630,431 | A | 5/1997 | Taylor |
| 5,636,634 | A | 6/1997 | Kordis et al. |
| 5,636,644 | A | 6/1997 | Hart et al. |
| 5,638,819 | A | 6/1997 | Manwaring et al. |
| 5,640,170 | A | 6/1997 | Anderson |
| 5,642,395 | A | 6/1997 | Anderton et al. |
| 5,643,175 | A | 7/1997 | Adair |
| 5,643,268 | A | 7/1997 | Vilsmeier et al. |
| 5,645,065 | A | 7/1997 | Shapiro et al. |
| 5,646,524 | A | 7/1997 | Gilboa |
| 5,646,525 | A | 7/1997 | Gilboa |
| 5,647,361 | A | 7/1997 | Damadian |
| 5,651,047 | A | 7/1997 | Moorman et al. |
| 5,660,865 | A | 8/1997 | Pedersen et al. |
| 5,662,108 | A | 9/1997 | Budd et al. |
| 5,662,111 | A | 9/1997 | Cosman |
| 5,664,001 | A | 9/1997 | Tachibana et al. |
| 5,674,296 | A | 10/1997 | Bryan et al. |
| 5,676,673 | A | 10/1997 | Ferre et al. |
| 5,681,260 | A | 10/1997 | Ueda et al. |
| 5,682,165 | A | 10/1997 | Lewis et al. |
| 5,682,886 | A | 11/1997 | Delp et al. |
| 5,682,890 | A | 11/1997 | Kormos et al. |
| 5,690,108 | A | 11/1997 | Chakeres |
| 5,694,945 | A | 12/1997 | Ben-Haim |
| 5,695,500 | A | 12/1997 | Taylor et al. |
| 5,695,501 | A | 12/1997 | Carol et al. |
| 5,696,500 | A | 12/1997 | Diem |
| 5,697,377 | A | 12/1997 | Wittkampf |
| 5,701,898 | A | 12/1997 | Adam et al. |
| 5,702,406 | A | 12/1997 | Vilsmeier et al. |
| 5,711,299 | A | 1/1998 | Manwaring et al. |
| 5,713,369 | A | 2/1998 | Tao et al. |
| 5,713,853 | A | 2/1998 | Clark et al. |
| 5,713,946 | A | 2/1998 | Ben-Haim |
| 5,715,822 | A | 2/1998 | Watkins et al. |
| 5,715,836 | A | 2/1998 | Kliegis et al. |
| 5,718,241 | A | 2/1998 | Ben-Haim et al. |
| 5,727,552 | A | 3/1998 | Ryan |
| 5,727,553 | A | 3/1998 | Saad |
| 5,729,129 | A | 3/1998 | Acker |
| 5,730,129 | A | 3/1998 | Darrow et al. |
| 5,730,130 | A | 3/1998 | Fitzpatrick et al. |
| 5,732,703 | A | 3/1998 | Kalfas et al. |
| 5,735,278 | A | 4/1998 | Hoult et al. |
| 5,738,096 | A | 4/1998 | Ben-Haim |

(56) References Cited

U.S. PATENT DOCUMENTS

| | | |
|---|---|---|
| 5,740,802 A | 4/1998 | Nafis et al. |
| 5,740,808 A | 4/1998 | Panescu et al. |
| 5,741,214 A | 4/1998 | Ouchi et al. |
| 5,741,320 A | 4/1998 | Thornton et al. |
| 5,742,394 A | 4/1998 | Hansen |
| 5,744,802 A | 4/1998 | Muehllehner et al. |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,752,518 A | 5/1998 | McGee et al. |
| 5,755,725 A | 5/1998 | Druais |
| RE35,816 E | 6/1998 | Schulz |
| 5,758,667 A | 6/1998 | Slettenmark |
| 5,760,335 A | 6/1998 | Gilboa |
| 5,762,064 A | 6/1998 | Polvani |
| 5,767,669 A | 6/1998 | Hansen et al. |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,050 A | 7/1998 | Chen et al. |
| 5,776,064 A | 7/1998 | Kalfas et al. |
| 5,782,765 A | 7/1998 | Jonkman |
| 5,782,828 A | 7/1998 | Chen et al. |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr et al. |
| 5,803,084 A | 9/1998 | Olson |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,820,591 A | 10/1998 | Thompson et al. |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,837,001 A | 11/1998 | Mackey |
| 5,840,024 A | 11/1998 | Taniguchi et al. |
| 5,840,025 A | 11/1998 | Ben-Haim |
| 5,842,984 A | 12/1998 | Avitall |
| 5,843,051 A | 12/1998 | Adams et al. |
| 5,843,076 A | 12/1998 | Webster, Jr. et al. |
| 5,846,183 A | 12/1998 | Chilcoat |
| 5,848,967 A | 12/1998 | Cosman |
| 5,851,183 A | 12/1998 | Bucholz |
| 5,853,327 A | 12/1998 | Gilboa |
| 5,857,997 A | 1/1999 | Cimino et al. |
| 5,865,726 A | 2/1999 | Katsurada et al. |
| 5,865,846 A | 2/1999 | Bryan et al. |
| 5,868,673 A | 2/1999 | Vesely |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,871,523 A | 2/1999 | Fleischman et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,134 A | 4/1999 | Goble et al. |
| 5,891,157 A | 4/1999 | Day et al. |
| 5,893,885 A | 4/1999 | Webster, Jr. |
| 5,899,860 A | 5/1999 | Pfeiffer et al. |
| 5,902,239 A | 5/1999 | Buurman |
| 5,902,324 A | 5/1999 | Thompson et al. |
| 5,904,691 A | 5/1999 | Barnett et al. |
| 5,907,395 A | 5/1999 | Schulz et al. |
| 5,909,476 A | 6/1999 | Cheng et al. |
| 5,913,820 A | 6/1999 | Bladen et al. |
| 5,916,210 A | 6/1999 | Winston |
| 5,919,147 A | 7/1999 | Jain |
| 5,919,188 A | 7/1999 | Shearon et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,930,329 A | 7/1999 | Navab |
| 5,935,160 A | 8/1999 | Auricchio et al. |
| 5,938,585 A | 8/1999 | Donofrio |
| 5,938,602 A | 8/1999 | Lloyd |
| 5,938,603 A | 8/1999 | Ponzi |
| 5,938,694 A | 8/1999 | Jaraczewski et al. |
| 5,941,251 A | 8/1999 | Panescu et al. |
| 5,944,023 A | 8/1999 | Johnson et al. |
| 5,947,925 A | 9/1999 | Ashiya et al. |
| 5,947,980 A | 9/1999 | Jensen et al. |
| 5,947,981 A | 9/1999 | Cosman |
| 5,950,629 A | 9/1999 | Taylor et al. |
| 5,951,461 A | 9/1999 | Nyo et al. |
| 5,951,475 A | 9/1999 | Gueziec et al. |
| 5,951,571 A | 9/1999 | Audette |
| 5,954,647 A | 9/1999 | Bova et al. |
| 5,954,649 A | 9/1999 | Chia et al. |
| 5,954,796 A | 9/1999 | McCarty et al. |
| 5,957,844 A | 9/1999 | Dekel et al. |
| 5,966,090 A | 10/1999 | McEwan |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,127 A | 11/1999 | Lax |
| 5,976,156 A | 11/1999 | Taylor et al. |
| 5,980,504 A | 11/1999 | Sharkey |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,724 A | 2/2000 | Gronningsaeter et al. |
| 6,019,725 A | 2/2000 | Vesely et al. |
| 6,019,728 A | 2/2000 | Iwata et al. |
| 6,022,578 A | 2/2000 | Miller |
| 6,024,695 A | 2/2000 | Taylor et al. |
| 6,024,739 A | 2/2000 | Ponzi et al. |
| 6,032,675 A | 3/2000 | Rubinsky |
| 6,035,229 A | 3/2000 | Silverstein et al. |
| 6,050,724 A | 4/2000 | Schmitz et al. |
| 6,059,718 A | 5/2000 | Taniguchi et al. |
| 6,061,588 A | 5/2000 | Thornton et al. |
| 6,063,022 A | 5/2000 | Ben-Haim |
| 6,064,390 A | 5/2000 | Sagar et al. |
| 6,071,288 A | 6/2000 | Carol et al. |
| 6,073,043 A | 6/2000 | Schneider |
| 6,076,008 A | 6/2000 | Bucholz |
| 6,077,257 A | 6/2000 | Edwards et al. |

(56) References Cited

U.S. PATENT DOCUMENTS

| | | |
|---|---|---|
| 6,096,036 A | 8/2000 | Bowe et al. |
| 6,096,050 A | 8/2000 | Audette |
| 6,104,294 A | 8/2000 | Andersson et al. |
| 6,104,944 A | 8/2000 | Martinelli |
| 6,106,517 A | 8/2000 | Zupkas |
| 6,112,111 A | 8/2000 | Glantz |
| 6,115,626 A | 9/2000 | Whayne et al. |
| 6,117,476 A | 9/2000 | Eger et al. |
| 6,118,845 A | 9/2000 | Simon et al. |
| 6,122,538 A | 9/2000 | Sliwa, Jr. et al. |
| 6,122,541 A | 9/2000 | Cosman et al. |
| 6,123,979 A | 9/2000 | Hepburn et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,171,303 B1 | 1/2001 | Ben-Haim et al. |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,179,809 B1 | 1/2001 | Khairkhahan et al. |
| 6,183,444 B1 | 2/2001 | Glines et al. |
| 6,188,355 B1 | 2/2001 | Gilboa |
| 6,192,280 B1 | 2/2001 | Sommer et al. |
| 6,194,639 B1 | 2/2001 | Botella et al. |
| 6,201,387 B1 | 3/2001 | Govari |
| 6,203,493 B1 | 3/2001 | Ben-Haim |
| 6,203,497 B1 | 3/2001 | Dekel et al. |
| 6,208,884 B1 | 3/2001 | Kumar et al. |
| 6,210,362 B1 | 4/2001 | Ponzi |
| 6,211,666 B1 | 4/2001 | Acker |
| 6,213,995 B1 | 4/2001 | Steen et al. |
| 6,213,998 B1 | 4/2001 | Shen et al. |
| 6,216,027 B1 | 4/2001 | Willis et al. |
| 6,216,029 B1 | 4/2001 | Paltieli |
| 6,223,067 B1 | 4/2001 | Vilsmeier et al. |
| 6,226,543 B1 | 5/2001 | Gilboa et al. |
| 6,233,310 B1 | 5/2001 | Relihan et al. |
| 6,233,476 B1 | 5/2001 | Strommer et al. |
| 6,236,875 B1 | 5/2001 | Bucholz et al. |
| 6,245,020 B1 | 6/2001 | Moore et al. |
| 6,246,231 B1 | 6/2001 | Ashe |
| 6,246,784 B1 | 6/2001 | Summers et al. |
| 6,246,898 B1 | 6/2001 | Vesely et al. |
| 6,246,899 B1 | 6/2001 | Chia et al. |
| 6,248,074 B1 | 6/2001 | Ohno et al. |
| 6,253,770 B1 | 7/2001 | Acker et al. |
| 6,259,942 B1 | 7/2001 | Westermann et al. |
| 6,264,654 B1 | 7/2001 | Swartz et al. |
| 6,272,371 B1 | 8/2001 | Shlomo |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,304,769 B1 | 10/2001 | Arenson et al. |
| 6,306,097 B1 | 10/2001 | Park et al. |
| 6,314,310 B1 | 11/2001 | Ben-Haim et al. |
| 6,319,250 B1 | 11/2001 | Falwell et al. |
| 6,331,116 B1 | 12/2001 | Kaufman et al. |
| 6,331,156 B1 | 12/2001 | Haefele et al. |
| 6,332,089 B1 | 12/2001 | Acker et al. |
| 6,335,617 B1 | 1/2002 | Osadchy et al. |
| 6,341,231 B1 | 1/2002 | Ferre et al. |
| 6,345,112 B1 | 2/2002 | Summers et al. |
| 6,346,940 B1 | 2/2002 | Fukunaga |
| 6,351,513 B1 | 2/2002 | Bani-Hashemi et al. |
| 6,351,659 B1 | 2/2002 | Vilsmeier |
| 6,366,799 B1 | 4/2002 | Acker et al. |
| 6,373,240 B1 | 4/2002 | Govari |
| 6,380,732 B1 | 4/2002 | Gilboa |
| 6,381,485 B1 | 4/2002 | Hunter et al. |
| 6,383,144 B1 | 5/2002 | Mooney et al. |
| 6,405,072 B1 | 6/2002 | Cosman |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,443,894 B1 | 9/2002 | Sumanaweera et al. |
| 6,445,943 B1 | 9/2002 | Ferre et al. |
| 6,447,504 B1 | 9/2002 | Ben-Haim et al. |
| 6,453,190 B1 | 9/2002 | Acker et al. |
| 6,468,265 B1 | 10/2002 | Evans et al. |
| 6,470,207 B1 | 10/2002 | Simon et al. |
| 6,473,635 B1 | 10/2002 | Rasche |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,484,118 B1 | 11/2002 | Govari |
| 6,490,475 B1 | 12/2002 | Seeley et al. |
| 6,493,573 B1 | 12/2002 | Martinelli et al. |
| 6,498,477 B1 | 12/2002 | Govari et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,517,534 B1 | 2/2003 | McGovern et al. |
| 6,527,443 B1 | 3/2003 | Vilsmeier et al. |
| 6,551,325 B2 | 4/2003 | Neubauer et al. |
| 6,558,333 B2 | 5/2003 | Gilboa et al. |
| 6,574,492 B1 | 6/2003 | Ben-Haim et al. |
| 6,574,498 B1 | 6/2003 | Gilboa |
| 6,580,938 B1 | 6/2003 | Acker |
| 6,584,174 B2 | 6/2003 | Schubert et al. |
| 6,585,763 B1 | 7/2003 | Keilman et al. |
| 6,591,129 B1 | 7/2003 | Ben-Haim et al. |
| 6,593,884 B1 | 7/2003 | Gilboa et al. |
| 6,609,022 B2 | 8/2003 | Vilsmeier et al. |
| 6,611,700 B1 | 8/2003 | Vilsmeier et al. |
| 6,615,155 B2 | 9/2003 | Gilboa |
| 6,618,612 B1 | 9/2003 | Acker et al. |
| 6,628,980 B2 | 9/2003 | Atalar et al. |
| 6,640,128 B2 | 10/2003 | Vilsmeier et al. |
| 6,650,927 B1 | 11/2003 | Keidar |
| 6,666,864 B2 | 12/2003 | Bencini et al. |
| 6,676,659 B2 | 1/2004 | Hutchins et al. |
| 6,690,816 B2 | 2/2004 | Aylward et al. |
| 6,690,963 B2 | 2/2004 | Ben-Haim et al. |
| 6,694,162 B2 | 2/2004 | Hartlep |
| 6,701,179 B1 | 3/2004 | Martinelli et al. |
| 6,702,780 B1 | 3/2004 | Gilboa et al. |
| 6,706,041 B1 | 3/2004 | Costantino |
| 6,711,429 B1 | 3/2004 | Gilboa et al. |
| 6,735,465 B2 | 5/2004 | Panescu |
| 6,751,492 B2 | 6/2004 | Ben-Haim |
| 6,770,070 B1 | 8/2004 | Balbierz |
| 6,788,967 B2 | 9/2004 | Ben-Haim et al. |
| 6,796,963 B2 | 9/2004 | Carpenter et al. |
| 6,810,281 B2 | 10/2004 | Brock et al. |
| 6,833,814 B2 | 12/2004 | Gilboa et al. |
| 6,887,236 B2 | 5/2005 | Gilboa |
| 6,947,788 B2 | 9/2005 | Gilboa et al. |
| 6,976,013 B1 | 12/2005 | Mah |
| 6,995,729 B2 | 2/2006 | Govari et al. |
| 6,996,430 B1 | 2/2006 | Gilboa et al. |
| 7,015,859 B2 | 3/2006 | Anderson |
| 7,033,325 B1 | 4/2006 | Sullivan |
| 7,158,754 B2 | 1/2007 | Anderson |
| 7,176,936 B2 | 2/2007 | Sauer et al. |
| 7,197,354 B2 | 3/2007 | Sobe |
| 7,233,820 B2 | 6/2007 | Gilboa |
| 7,236,567 B2 | 6/2007 | Sandkamp et al. |
| 7,286,868 B2 | 10/2007 | Govari |
| 7,301,332 B2 | 11/2007 | Govari et al. |
| 7,321,228 B2 | 1/2008 | Govari |
| 7,324,915 B2 | 1/2008 | Altmann et al. |
| 7,343,195 B2 | 3/2008 | Strommer et al. |
| 7,353,125 B2 | 4/2008 | Nieminen et al. |
| 7,357,795 B2 | 4/2008 | Kaji et al. |
| 7,366,562 B2 | 4/2008 | Dukesherer et al. |
| 7,370,656 B2 | 5/2008 | Gleich et al. |

(56) References Cited

U.S. PATENT DOCUMENTS

| | | |
|---|---|---|
| 7,373,271 B1 | 5/2008 | Schneider |
| 7,386,339 B2 | 6/2008 | Strommer et al. |
| 7,397,364 B2 | 7/2008 | Govari |
| 7,399,296 B2 | 7/2008 | Poole et al. |
| 7,420,468 B2 | 9/2008 | Fabian et al. |
| 7,497,029 B2 | 3/2009 | Plassky et al. |
| 7,505,809 B2 | 3/2009 | Strommer et al. |
| 7,517,318 B2 | 4/2009 | Altmann et al. |
| 7,536,218 B2 | 5/2009 | Govari et al. |
| 7,555,330 B2 | 6/2009 | Gilboa et al. |
| RE40,852 E | 7/2009 | Martinelli et al. |
| 7,570,987 B2 | 8/2009 | Raabe et al. |
| 7,577,474 B2 | 8/2009 | Vilsmeier |
| 7,579,837 B2 | 8/2009 | Fath et al. |
| 7,587,235 B2 | 9/2009 | Wist et al. |
| 7,599,535 B2 | 10/2009 | Kiraly et al. |
| 7,599,810 B2 | 10/2009 | Yamazaki |
| 7,630,753 B2 | 12/2009 | Simon et al. |
| 7,634,122 B2 | 12/2009 | Bertram et al. |
| 7,636,595 B2 | 12/2009 | Marquart et al. |
| 7,641,609 B2 | 1/2010 | Ohnishi et al. |
| 7,648,458 B2 | 1/2010 | Niwa et al. |
| 7,652,468 B2 | 1/2010 | Kruger et al. |
| 7,652,578 B2 | 1/2010 | Braun et al. |
| 7,657,300 B2 | 2/2010 | Hunter et al. |
| 7,659,912 B2 | 2/2010 | Akimoto et al. |
| 7,660,623 B2 | 2/2010 | Hunter et al. |
| 7,680,528 B2 | 3/2010 | Pfister et al. |
| 7,684,849 B2 | 3/2010 | Wright et al. |
| 7,686,767 B2 | 3/2010 | Maschke |
| 7,688,064 B2 | 3/2010 | Shalgi et al. |
| 7,696,899 B2 | 4/2010 | Immerz et al. |
| 7,697,973 B2 | 4/2010 | Strommer et al. |
| 7,697,974 B2 | 4/2010 | Jenkins et al. |
| 7,720,517 B2 | 5/2010 | Drysen |
| 7,722,565 B2 | 5/2010 | Wood et al. |
| 7,725,154 B2 | 5/2010 | Beck et al. |
| 7,725,164 B2 | 5/2010 | Suurmond et al. |
| 7,727,269 B2 | 6/2010 | Abraham-Fuchs et al. |
| 7,729,742 B2 | 6/2010 | Govari |
| 7,744,605 B2 | 6/2010 | Vilsmeier et al. |
| 7,747,307 B2 | 6/2010 | Wright et al. |
| 7,751,865 B2 | 7/2010 | Jascob et al. |
| 7,782,046 B2 | 8/2010 | Anderson |
| 7,782,189 B2 | 8/2010 | Spoonhower et al. |
| 7,784,468 B2 | 8/2010 | Fabian et al. |
| 7,831,076 B2 | 11/2010 | Altmann et al. |
| 7,905,827 B2 | 3/2011 | Uchiyama et al. |
| 7,912,662 B2 | 3/2011 | Zuhars et al. |
| 7,969,143 B2 | 6/2011 | Gilboa |
| 8,692,707 B2 | 4/2014 | Lee et al. |
| 9,575,140 B2 | 2/2017 | Zur |
| 9,675,424 B2 | 6/2017 | Jascob et al. |
| 10,722,311 B2 | 7/2020 | Koyrakh et al. |
| 10,751,126 B2 * | 8/2020 | Koyrakh ............... A61B 34/20 |
| 2001/0007918 A1 | 7/2001 | Vilsmeier et al. |
| 2001/0031919 A1 | 10/2001 | Strommer et al. |
| 2001/0034530 A1 | 10/2001 | Malackowski et al. |
| 2001/0036245 A1 | 11/2001 | Kienzle et al. |
| 2001/0038705 A1 | 11/2001 | Rubbert et al. |
| 2002/0022837 A1 | 2/2002 | Mazzocchi et al. |
| 2002/0045916 A1 | 4/2002 | Gray et al. |
| 2002/0045919 A1 | 4/2002 | Johansson-Ruden et al. |
| 2002/0065461 A1 | 5/2002 | Cosman |
| 2002/0082498 A1 | 6/2002 | Wendt et al. |
| 2002/0095081 A1 | 7/2002 | Vilsmeier |
| 2002/0128565 A1 | 9/2002 | Rudy |
| 2002/0137014 A1 | 9/2002 | Anderson et al. |
| 2002/0143324 A1 | 10/2002 | Edwards |
| 2002/0165448 A1 | 11/2002 | Ben-Haim et al. |
| 2002/0173689 A1 | 11/2002 | Kaplan |
| 2002/0193686 A1 | 12/2002 | Gilboa |
| 2003/0018251 A1 | 1/2003 | Solomon |
| 2003/0074011 A1 | 4/2003 | Gilboa et al. |
| 2003/0086599 A1 | 5/2003 | Armato, III et al. |
| 2003/0099390 A1 | 5/2003 | Zeng et al. |
| 2003/0142753 A1 | 7/2003 | Gunday |
| 2003/0144658 A1 | 7/2003 | Schwartz et al. |
| 2003/0160721 A1 | 8/2003 | Gilboa et al. |
| 2003/0184285 A1 | 10/2003 | Anderson et al. |
| 2003/0216639 A1 | 11/2003 | Gilboa et al. |
| 2004/0006268 A1 | 1/2004 | Gilboa et al. |
| 2004/0015049 A1 | 1/2004 | Zaar |
| 2004/0019350 A1 | 1/2004 | O'Brien et al. |
| 2004/0024309 A1 | 2/2004 | Ferre et al. |
| 2004/0086161 A1 | 5/2004 | Sivaramakrishna et al. |
| 2004/0097804 A1 | 5/2004 | Sobe |
| 2004/0102696 A1 | 5/2004 | Govari |
| 2004/0116803 A1 | 6/2004 | Jascob et al. |
| 2004/0122310 A1 | 6/2004 | Lim |
| 2004/0138548 A1 | 7/2004 | Strommer et al. |
| 2004/0143317 A1 | 7/2004 | Stinson et al. |
| 2004/0169509 A1 | 9/2004 | Czipott et al. |
| 2004/0215181 A1 | 10/2004 | Christopherson et al. |
| 2004/0249267 A1 | 12/2004 | Gilboa |
| 2004/0254454 A1 | 12/2004 | Kockro |
| 2005/0018885 A1 | 1/2005 | Chen et al. |
| 2005/0027193 A1 | 2/2005 | Mitschke et al. |
| 2005/0033149 A1 | 2/2005 | Strommer et al. |
| 2005/0059890 A1 | 3/2005 | Deal et al. |
| 2005/0085715 A1 | 4/2005 | Dukesherer et al. |
| 2005/0085720 A1 | 4/2005 | Jascob et al. |
| 2005/0090818 A1 | 4/2005 | Pike et al. |
| 2005/0107687 A1 | 5/2005 | Anderson |
| 2005/0107688 A1 | 5/2005 | Strommer |
| 2005/0119527 A1 | 6/2005 | Banik et al. |
| 2005/0182295 A1 | 8/2005 | Soper et al. |
| 2005/0197566 A1 | 9/2005 | Strommer et al. |
| 2005/0222793 A1 | 10/2005 | Lloyd et al. |
| 2005/0272971 A1 | 12/2005 | Ohnishi et al. |
| 2006/0015126 A1 | 1/2006 | Sher |
| 2006/0025677 A1 | 2/2006 | Verard et al. |
| 2006/0036151 A1 | 2/2006 | Ferre et al. |
| 2006/0058647 A1 | 3/2006 | Strommer et al. |
| 2006/0064006 A1 | 3/2006 | Strommer et al. |
| 2006/0079759 A1 | 4/2006 | Vaillant et al. |
| 2006/0084867 A1 | 4/2006 | Tremblay et al. |
| 2006/0116575 A1 | 6/2006 | Willis |
| 2006/0149134 A1 | 7/2006 | Soper et al. |
| 2006/0181271 A1 | 8/2006 | Lescourret |
| 2006/0208725 A1 | 9/2006 | Tapson |
| 2006/0241396 A1 | 10/2006 | Fabian et al. |
| 2006/0241399 A1 | 10/2006 | Fabian |
| 2007/0163597 A1 | 7/2007 | Mikkaichi et al. |
| 2007/0167714 A1 | 7/2007 | Kiraly et al. |
| 2007/0167738 A1 | 7/2007 | Timinger et al. |
| 2007/0167743 A1 | 7/2007 | Honda et al. |
| 2007/0167804 A1 | 7/2007 | Park et al. |
| 2007/0167806 A1 | 7/2007 | Wood et al. |
| 2007/0225553 A1 | 9/2007 | Shahidi |
| 2007/0232898 A1 | 10/2007 | Huynh et al. |
| 2007/0265639 A1 | 11/2007 | Danek et al. |
| 2007/0287901 A1 | 12/2007 | Strommer et al. |
| 2008/0008368 A1 | 1/2008 | Matsumoto |
| 2008/0018468 A1 | 1/2008 | Volpi et al. |
| 2008/0033452 A1 | 2/2008 | Vetter et al. |
| 2008/0086051 A1 | 4/2008 | Voegele |
| 2008/0097154 A1 | 4/2008 | Makower et al. |
| 2008/0097156 A1 | 4/2008 | Nakamura |
| 2008/0097187 A1 | 4/2008 | Gielen et al. |
| 2008/0118135 A1 | 5/2008 | Averbuch et al. |
| 2008/0132909 A1 | 6/2008 | Jascob et al. |
| 2008/0132911 A1 | 6/2008 | Sobe |
| 2008/0139886 A1 | 6/2008 | Tatsuyama |
| 2008/0139915 A1 | 6/2008 | Dolan et al. |
| 2008/0144909 A1 | 6/2008 | Wiemker et al. |
| 2008/0147000 A1 | 6/2008 | Seibel et al. |
| 2008/0154172 A1 | 6/2008 | Mauch |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0188749 A1 | 8/2008 | Rasche et al. |
| 2008/0247622 A1 | 10/2008 | Aylward et al. |

(56) References Cited

U.S. PATENT DOCUMENTS

| | | |
|---|---|---|
| 2008/0249395 A1 | 10/2008 | Shachar et al. |
| 2008/0284554 A1 | 11/2008 | Schroeder et al. |
| 2008/0294034 A1 | 11/2008 | Krueger et al. |
| 2009/0027258 A1 | 1/2009 | Stayton |
| 2009/0082665 A1 | 3/2009 | Anderson |
| 2009/0182224 A1 | 7/2009 | Shmarak et al. |
| 2009/0189820 A1 | 7/2009 | Saito et al. |
| 2009/0287443 A1 | 11/2009 | Jascob et al. |
| 2009/0318797 A1 | 12/2009 | Hadani |
| 2011/0085720 A1 | 4/2011 | Averbuch |
| 2012/0323111 A1 | 12/2012 | Jain et al. |
| 2015/0035697 A1 | 2/2015 | Cho |
| 2018/0116722 A1 | 5/2018 | Koyrakh |

FOREIGN PATENT DOCUMENTS

| | | |
|---|---|---|
| CN | 103945772 A | 7/2014 |
| CN | 104983386 A | 10/2015 |
| DE | 3508730 A1 | 9/1986 |
| DE | 3520782 A1 | 12/1986 |
| DE | 3717871 A1 | 12/1988 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19715202 A1 | 10/1998 |
| DE | 19751761 A1 | 10/1998 |
| DE | 19832296 A1 | 2/1999 |
| DE | 19747427 A1 | 5/1999 |
| DE | 10085137 T1 | 11/2002 |
| EP | 0062941 A1 | 10/1982 |
| EP | 0119660 A1 | 9/1984 |
| EP | 0155857 A2 | 9/1985 |
| EP | 0319844 A1 | 6/1989 |
| EP | 0326768 A2 | 8/1989 |
| EP | 0350996 A1 | 1/1990 |
| EP | 0456103 A2 | 11/1991 |
| EP | 0581704 A1 | 2/1994 |
| EP | 0600610 A2 | 6/1994 |
| EP | 0655138 B1 | 5/1995 |
| EP | 0796633 A1 | 9/1997 |
| EP | 0829229 A1 | 3/1998 |
| EP | 0894473 A2 | 2/1999 |
| EP | 0908146 A2 | 4/1999 |
| EP | 0922966 A2 | 6/1999 |
| EP | 0930046 A2 | 7/1999 |
| EP | 1078644 A1 | 2/2001 |
| EP | 2096523 A1 | 9/2009 |
| FR | 2618211 A1 | 1/1989 |
| GB | 2094590 A | 9/1982 |
| GB | 2164856 A | 4/1986 |
| GB | 2197078 A | 5/1988 |
| JP | 03267054 A | 11/1991 |
| JP | 06194639 A | 7/1994 |
| JP | H0792016 A | 4/1995 |
| JP | 3025752 B2 | 3/2000 |
| JP | 2000512005 A | 9/2000 |
| JP | 2002122409 A | 4/2002 |
| JP | 2005185845 A | 7/2005 |
| JP | 2006170781 A | 6/2006 |
| WO | 8809151 A1 | 12/1988 |
| WO | 8905123 A1 | 6/1989 |
| WO | 9005494 A1 | 5/1990 |
| WO | 9103982 A1 | 4/1991 |
| WO | 9104711 A1 | 4/1991 |
| WO | 9107726 A1 | 5/1991 |
| WO | 9203090 A1 | 3/1992 |
| WO | 9206645 A1 | 4/1992 |
| WO | 9404938 A1 | 3/1994 |
| WO | 9423647 A1 | 10/1994 |
| WO | 9424933 A1 | 11/1994 |
| WO | 9507055 A1 | 3/1995 |
| WO | 9509562 A1 | 4/1995 |
| WO | 9605768 A1 | 2/1996 |
| WO | 9611624 A2 | 4/1996 |
| WO | 9632059 A1 | 10/1996 |
| WO | 9641119 A1 | 12/1996 |
| WO | 9700011 A1 | 1/1997 |
| WO | 9700054 A1 | 1/1997 |
| WO | 9700058 A1 | 1/1997 |
| WO | 9700059 A1 | 1/1997 |
| WO | 9700308 A1 | 1/1997 |
| WO | 9702650 A1 | 1/1997 |
| WO | 9725101 A2 | 7/1997 |
| WO | 97/29684 A1 | 8/1997 |
| WO | 9729682 A1 | 8/1997 |
| WO | 9729685 A1 | 8/1997 |
| WO | 9729701 A1 | 8/1997 |
| WO | 9729709 A1 | 8/1997 |
| WO | 9736143 A1 | 10/1997 |
| WO | 9736192 A1 | 10/1997 |
| WO | 9742517 A1 | 11/1997 |
| WO | 9744089 A1 | 11/1997 |
| WO | 1997042517 A1 | 11/1997 |
| WO | 9749453 A1 | 12/1997 |
| WO | 9800034 A2 | 1/1998 |
| WO | 9808554 A1 | 3/1998 |
| WO | 9811840 A1 | 3/1998 |
| WO | 9829032 A1 | 7/1998 |
| WO | 9835720 A2 | 8/1998 |
| WO | 9838908 A1 | 9/1998 |
| WO | 9848722 A1 | 11/1998 |
| WO | 9915097 A2 | 4/1999 |
| WO | 9916350 A1 | 4/1999 |
| WO | 9921498 A1 | 5/1999 |
| WO | 9923956 A1 | 5/1999 |
| WO | 9926549 A1 | 6/1999 |
| WO | 9926826 A2 | 6/1999 |
| WO | 9927839 A2 | 6/1999 |
| WO | 9929253 A1 | 6/1999 |
| WO | 9930777 A1 | 6/1999 |
| WO | 99/32033 A1 | 7/1999 |
| WO | 9933406 A1 | 7/1999 |
| WO | 9937208 A1 | 7/1999 |
| WO | 9938449 A1 | 8/1999 |
| WO | 9952094 A1 | 10/1999 |
| WO | 9955415 A1 | 11/1999 |
| WO | 9960939 A1 | 12/1999 |
| WO | 0006701 A1 | 2/2000 |
| WO | 0010456 A1 | 3/2000 |
| WO | 0016684 A1 | 3/2000 |
| WO | 0035531 A1 | 6/2000 |
| WO | 0106917 A1 | 2/2001 |
| WO | 0112057 A1 | 2/2001 |
| WO | 0130437 A1 | 5/2001 |
| WO | 0167035 A1 | 9/2001 |
| WO | 0187136 A2 | 11/2001 |
| WO | 0191842 A1 | 12/2001 |
| WO | 02064011 A2 | 8/2002 |
| WO | 02070047 A1 | 9/2002 |
| WO | 03086498 A2 | 10/2003 |
| WO | 2004/023986 A1 | 3/2004 |
| WO | 2006116597 A2 | 11/2006 |
| WO | 2015164171 A1 | 10/2015 |

OTHER PUBLICATIONS

Extended European Search Report issued in corresponding Appl. No. EP 17863634.6 dated Apr. 23, 2020 (8 pages).

Australian Examination Report issued in Australian Patent Application No. 2017348161 dated Apr. 22, 2022.

The Second Office Action issued in Chinese Patent Application No. 201780066962.9 dated Sep. 23, 2021, with English translation.

The First Office Action issued in Chinese Application No. 201780066962.9 dated Feb. 26, 2021, with English translation, 17 pages.

Notice of Reasons for Rejection issued in Japanese Office Action dated Jul. 20, 2021, with English translation, 12 pages.

* cited by examiner

SYSTEM AND METHOD FOR IDENTIFYING A LOCATION AND/OR AN ORIENTATION OF AN ELECTROMAGNETIC SENSOR BASED ON A MAP

CROSS-REFERENCE TO RELATED APPLICATIONS

This application is a continuation of U.S. patent application Ser. No. 15/337,166, filed on Oct. 28, 2016.

INTRODUCTION

The present disclosure generally relates to electromagnetic navigation, and more particularly to systems and methods for generating a map for electromagnetic navigation and identifying a location and/or an orientation of a sensor based on the map.

BACKGROUND

Electromagnetic navigation (EMN) has helped expand medical imaging, diagnosis, prognosis, and treatment capabilities by enabling a location and/or an orientation of a medical device and/or of a target of interest to be accurately determined within a patient's body. Generally, an antenna generates an electromagnetic (EM) field in an EM volume, a sensor incorporated onto a medical device senses an EM signal or strength based on the field, and the EMN system identifies a sensor location based on the sensed EM strength. The EM strength at each location in the EM volume is previously measured or mapped to enable the sensor location to be identified in the EM volume by comparing the sensed EM strength and the previously measured EM strength.

In some cases, it may be desirable for the sensor to be a small-sized sensor, such as a single-coil sensor, because, for instance, a small sized sensor may be navigable to additional locations (e.g., narrower portions of a luminal network) within the patient, to which a larger-sized sensor may not be navigable. Additionally, in contrast to large-size sensors which sometimes must be removed from the patient during a procedure to make room in a working channel for other tools, the small-sized sensor may remain within the patient throughout the procedure without interfering with the other tools, thereby facilitating EMN functionality throughout the procedure.

To enable a small-sized sensor such as a single-coil sensor to be accurately located within an EM volume, it may be necessary to generate multiple (for instance, 6 or more) geometrically diverse EM fields within the EM volume. However, because each of the EM fields would require generation of a measured mapping of the corresponding EM strength at each location in the EM volume, increasing the number of EM fields would increase the number of mappings, which can be time consuming and laborious. Additionally, to improve the accuracy with which the sensor location can be determined, precise measurements at many (for example, thousands) of gridpoints within the EM volume may be needed, which could make the generating of the mapping even more time consuming. Also, because of the potential variability during the manufacturing processes and tolerances of electrical equipment, the mapping process may need to be completed for each new antenna that is produced and for each electromagnetic navigation system installation.

Given the foregoing, a need exists for improved systems and methods for generating a map for electromagnetic navigation and identifying a location and/or an orientation of a sensor based on the map.

SUMMARY

The present disclosure is related to systems and methods for generating a map of EM field strength, for example, a high density (HD) map, for electromagnetic navigation and identifying a sensor location and/or orientation based on the map. In one example, the HD map has a greater (e.g., finer) gridpoint resolution (that is, more gridpoints) in the EM volume than that of a low density (LD) grid in the EM volume according to which EM field strength measurements are taken and stored in a LD map. The HD map, in some aspects, is generated based on the previously generated LD map of measured EM field strength and also based on EM field strength calculations based, for instance on geometric configurations of antennas in an antenna assembly. In this manner, the location and/or the orientation of the sensor navigated within the patient's body can be accurately identified without the need to take EM field strength measurements at each of the many gridpoints of the HD map within the EM volume. This can enable the use of a small-sized sensor in EMN procedures while minimizing any increased burden of map generation.

In accordance with one aspect of the present disclosure, a method is provided for generating a high density (HD) map for identifying a location and/or an orientation of an electromagnetic (EM) sensor within an EM volume in which an EM field is generated by way of an antenna assembly. The method includes receiving a measured EM field strength at each gridpoint of a first set of gridpoints of the EM volume from a measurement device. An EM field strength at each gridpoint of a second set of gridpoints of the EM volume is calculated based on a geometric configuration of an antenna of the antenna assembly. The HD map is generated based on the measured EM field strength at each gridpoint of the first set of gridpoints and the calculated EM field strength at each gridpoint of the second set of gridpoints.

In another aspect of the present disclosure, the antenna assembly generates at least six EM waveforms as components of the EM field.

In a further aspect of the present disclosure, the EM field strength is calculated along a three axes coordinate system for each of the at least six EM waveforms.

In yet another aspect of the present disclosure, the EM field strength is measured by way of a sensor having three coils corresponding to the three axes, respectively.

In still another aspect of the present disclosure, the second set of gridpoints includes each gridpoint of the first set of gridpoints.

In another aspect of the present disclosure, the generating the HD map includes calculating an error between the measured EM field strength and the calculated EM field strength, at each gridpoint of the first set of gridpoints. An error for each gridpoint of the second set of gridpoints is interpolated based on the calculated error at each gridpoint of the first set of gridpoints. The interpolated error and the calculated EM field strength at each gridpoint of the second set of gridpoints are added to generate the HD map In a further aspect of the present disclosure, the error is calculated based on a difference between the measured EM field strength and the calculated EM field strength at each gridpoint of the first set of gridpoints.

In yet another aspect of the present disclosure, the error is based on at least one of an L1 or L2 norm of differences between the measured EM field strength and the calculated EM field strength along the three axes.

In still another aspect of the present disclosure, the method further includes calculating a pseudo-inverse of the calculated EM field strength at each gridpoint of the second set of gridpoints.

In another aspect of the present disclosure, the HD map further includes the pseudo-inverse of the calculated EM field strength at each gridpoint of the second plurality of gridpoints.

In accordance with another aspect of the present disclosure an apparatus is provided for generating an HD map for identifying a location and/or an orientation of an EM sensor within an EM volume in which an EM field is generated by way of an antenna assembly. The apparatus includes a processor and a memory storing processor-executable instructions that, when executed by the processor, cause the processor to receive, from a measurement device, a measured EM field strength at each gridpoint of a first set of gridpoints of the EM volume. An EM field strength at each gridpoint of a second set of gridpoints of the EM volume is calculated based on a geometric configuration of at least one antenna of the antenna assembly. The HD map is generated based on the measured EM field strength at each gridpoint of the first set of gridpoints and the calculated EM field strength at each gridpoint of the second set of gridpoints.

In another aspect of the present disclosure, the antenna assembly generates at least six EM waveforms as components of the EM field.

In still another aspect of the present disclosure, the EM field strength is calculated along a three axes coordinate system for each of the at least six EM waveforms.

In a further aspect of the present disclosure, the EM field strength is measured with a sensor having three coils corresponding to the three axes, respectively.

In yet another aspect of the present disclosure, the second set of gridpoints includes each gridpoint of the first set of gridpoints.

In another aspect of the present disclosure, the generating of the HD map includes calculating an error between the measured EM field strength and the calculated EM field strength, at each gridpoint of the first set of gridpoints. An error for each gridpoint of the second plurality of gridpoints is interpolated based on the calculated error at each gridpoint of the first plurality of gridpoint. The interpolated error and the calculated EM field strength at each gridpoint of the second plurality of gridpoints are added to generate the HD map.

In yet another aspect of the present disclosure, the error is calculated based on a difference between the measured EM field strength and the calculated EM field strength at each gridpoint of the first set of gridpoints.

In a further aspect of the present disclosure, the error is based on an L1 and/or L2 norm of differences between the measured EM field strength and the calculated EM field strength along the three axes.

In still another aspect of the present disclosure, the memory further stores instructions that, when executed by the processor, cause the processor to calculate a pseudo-inverse of the calculated EM field strength at each gridpoint of the second set of gridpoints.

In another aspect of the present disclosure, the HD map further includes the pseudo-inverse of the calculated EM field strength at each gridpoint of the second set of gridpoints.

In accordance with another aspect of the present disclosure, a method is provided for identifying a location and/or an orientation of an EM sensor navigated within an EM volume. The method includes retrieving, from a memory, a calculated EM field strength at each gridpoint of a second set of gridpoints of the EM volume. An EM field is generated by way of an antenna assembly. A measured EM field strength is received from the EM sensor. A first gridpoint among a first set of gridpoints of the EM volume is identified based on the measured EM field strength and a HD map. The location and/or the orientation of the EM sensor are identified based on the HD map, using the first gridpoint as an initial condition. The second set of gridpoints includes the first plurality of gridpoints.

In another aspect of the present disclosure, the antenna assembly includes at least six antennas, each of the antennas including multiple loops.

In yet another aspect of the present disclosure, the multiple loops have a geometric configuration.

In a further aspect of the present disclosure, the HD map includes a calculated EM field strength for each gridpoint of the second set of gridpoints in the EM volume.

In still another aspect of the present disclosure, the calculated EM field strength is based on the respective geometric configurations of the at least six antennas.

In another aspect of the present disclosure, the HD map further includes a pseudo-inverse of the calculated EM field strength at each gridpoint of the second plurality of gridpoints.

In yet another aspect of the present disclosure, the identifying the first gridpoint includes identifying an orientation vector $\vec{n}_{(a,b,c)}$, where (a,b,c) is a gridpoint in the first set of gridpoints, satisfying the following condition: $\vec{n}_{(a,b,c)} \approx \vec{B}_{(a,b,c)}^{-1} \cdot V$, where $\vec{B}_{(d,e,f)}^{-1}$ is a pseudo-inverse of $\vec{B}_{(a,b,c)}$, which is a calculated EM field strength at gridpoint (a,b,c) in the HD map. A difference between $\vec{B}_{(a,b,c)} \cdot \vec{n}_{(a,b,c)}$ and V is calculating. A gridpoint (A,B,C), from among the first set of gridpoints, where a difference between $\vec{B}_{(ABc)} \cdot \vec{n}$ and V is the smallest, is selected, as the first gridpoint.

In a further aspect of the present disclosure, the identifying the location and/or the orientation includes identifying an orientation vector $\vec{n}_{(d,e,f)}$, where (d,e,f) is a gridpoint in the second set of gridpoints and is located nearby (e.g. within a predetermined distance) from the first gridpoint (A,B,C), satisfying the following condition: $\vec{n}_{(d,e,f)} \approx \vec{B}_{(d,e,f)}^{-1} \cdot V$, where $\vec{B}_{(d,e,f)}^{-1}$ is a pseudo-inverse of $\vec{B}_{(d,e,f)}$, which is a calculated EM field strength at gridpoint (d,e,f) in the HD map. A difference between $\vec{B}_{(d,e,f)} \cdot \vec{n}_{(d,e,f)}$ and V is calculated. A second gridpoint (D,E,F) from among the second set of gridpoints, where a difference between $\vec{B}_{(D,E,F)} \cdot \vec{n}_{(D,E,F)}$ and V is the smallest, is selected.

In still another aspect of the present disclosure, $\vec{n}_{(D,E,F)}$ is related to the orientation of the EM sensor.

In another aspect of the present disclosure, the second gridpoint (D,E,F) is the location of the EM sensor.

In accordance with another aspect of the present disclosure, a system is provided for identifying a location and/or an orientation of an EM sensor navigated within an EM volume. The system includes an antenna assembly, the EM sensor, a processor, and a memory. The antenna assembly is configured to radiate an EM field within the EM volume. The EM sensor is configured to measure an EM field strength based on the radiated EM field. The memory stores a calculated EM field strength at each gridpoint of a second set of gridpoints of the EM volume. The memory also stores processor-executable instructions that, when executed by the processor, cause the processor to retrieve, from the memory, the calculated EM field strength at each gridpoint of the second set of gridpoints. A first gridpoint among a first set of gridpoints of the EM volume is identified based on the measured EM field strength and the HD map. The location and/or the orientation of the EM sensor are identified based on the HD map, using the first gridpoint as an initial condition. The second set of gridpoints includes the first set of gridpoints.

In a further aspect of the present disclosure, the antenna assembly includes at least six antennas, each of the antennas including a plurality of loops.

In still another aspect of the present disclosure, the plurality of loops has a geometric configuration.

In another aspect of the present disclosure, the HD map includes a calculated EM field strength at each gridpoint of the second set of gridpoints in the EM volume.

In yet another aspect of the present disclosure, the calculated EM field strength is based on the respective geometric configurations of the at least six antennas.

In another aspect of the present disclosure, the HD map further includes a pseudo-inverse of the calculated EM field strength at each gridpoint of the second set of gridpoints.

In another aspect of the present disclosure, the identifying the first gridpoint includes identifying an orientation vector $\vec{n}_{(a,b,c)}$, where $(a,b,c)$ is a gridpoint in the first set of gridpoints, satisfying the following condition: $\vec{n}_{(a,b,c)} \approx \vec{B}_{(a,b,c)}^{-1} \cdot V$, where $\vec{B}_{(d,e,f)}^{-1}$ is a pseudo-inverse of $\vec{B}_{(a,b,c)}$, which is a calculated EM field strength at gridpoint $(a,b,c)$ in the HD map. A difference between $\vec{B}_{(a,b,c)} \cdot \vec{n}_{(a,b,c)}$ and V is calculated. A gridpoint $(A,B,C)$ from among the first plurality of gridpoints, where a difference between $\vec{B}_{(A,B,C)} \cdot \vec{n}$ and V is the smallest, is selected as the first gridpoint.

In yet another aspect of the present disclosure, the identifying the location and/or the orientation includes identifying an orientation vector $\vec{n}_{(d,e,f)}$, where $(d,e,f)$ is a gridpoint in the second set of gridpoints and is located nearby (e.g., within a predetermined distance from) the first gridpoint $(A,B,C)$, satisfying the following condition: $\vec{n}_{(d,e,f)} \approx \vec{B}_{(d,e,f)}^{-1} \cdot V$, where $\vec{B}_{(d,e,f)}^{-1}$ is a pseudo-inverse of $\vec{B}_{(d,e,f)}$, which is a calculated EM field strength at gridpoint $(d,e,f)$ in the HD map. A difference between $\vec{B}_{(d,e,f)} \cdot \vec{n}_{(d,e,f)}$ and V is calculated. A second gridpoint $(D,E,F)$ from among the second plurality of gridpoints, where a difference between $\vec{B}_{(D,E,F)} \cdot \vec{n}_{(D,E,F)}$ and V is the smallest is selected.

In another aspect of the present disclosure, $\vec{n}_{(D,E,F)}$ is related to the orientation of the EM sensor.

In a further aspect of the present disclosure, the second gridpoint $(D,E,F)$ is the location of the EM sensor.

Any of the aspects and embodiments of the present disclosure may be combined without departing from the scope of the present disclosure.

BRIEF DESCRIPTION OF THE DRAWINGS

Objects and features of the presently disclosed systems and methods will become apparent to those of ordinary skill in the art when descriptions of various embodiments are read with reference to the accompanying drawings, of which.

DETAILED DESCRIPTION

The present disclosure is related to systems and methods for generating a high density (HD) map and identifying a location and/or an orientation of a sensor, which may include at least one coil, based on the HD map. In some aspects, the respective geometric configurations the antennas enable automated and highly repeatable processes for reproducing such antennas and/or for mathematically calculating the expected or theoretical EM strength at every HD gridpoint within an EM volume (for instance, where the antennas have geometric configurations based on linear portions of printed circuit board (PCB) traces, which facilitate use of the superposition principle in computing the total contribution of the fields generated by way of each antenna to the total combined EM field within the volume). These mathematical calculations may be combined with actual measurements made in a coarse coordinate system, which includes fewer gridpoints than the number of gridpoints used for the mathematically calculated EM strength. In this way, the time and/or cost related to making the measurements can be lowered and a HD map can be generated and used in a repeatable, efficient, and cost-effective manner.

Further, the present disclosure is related to systems and methods for identifying a location and/or an orientation of an EM sensor by using the HD map. In general, the EM sensor senses EM strengths, and an EMN system compares the sensed EM strengths with the expected EM strengths of the HD map and identifies the location and the orientation of the EM sensor.

In an aspect of the present disclosure, a fine coordinate system (e.g., a HD coordinate system or set of gridpoints) is used to describe a coordinate system of the EM volume, which includes more gridpoints than those in a coarse coordinate system (e.g., a LD coordinate system or set of gridpoints) of the EM volume. In some aspects, every gridpoint of the coarse coordinate system may be included in the fine coordinate system. In general, the coarse coordinate system is utilized for actual EM field strength measurements and the fine coordinate system is utilized for mathematical calculations of EM field strength.

Figure 1:
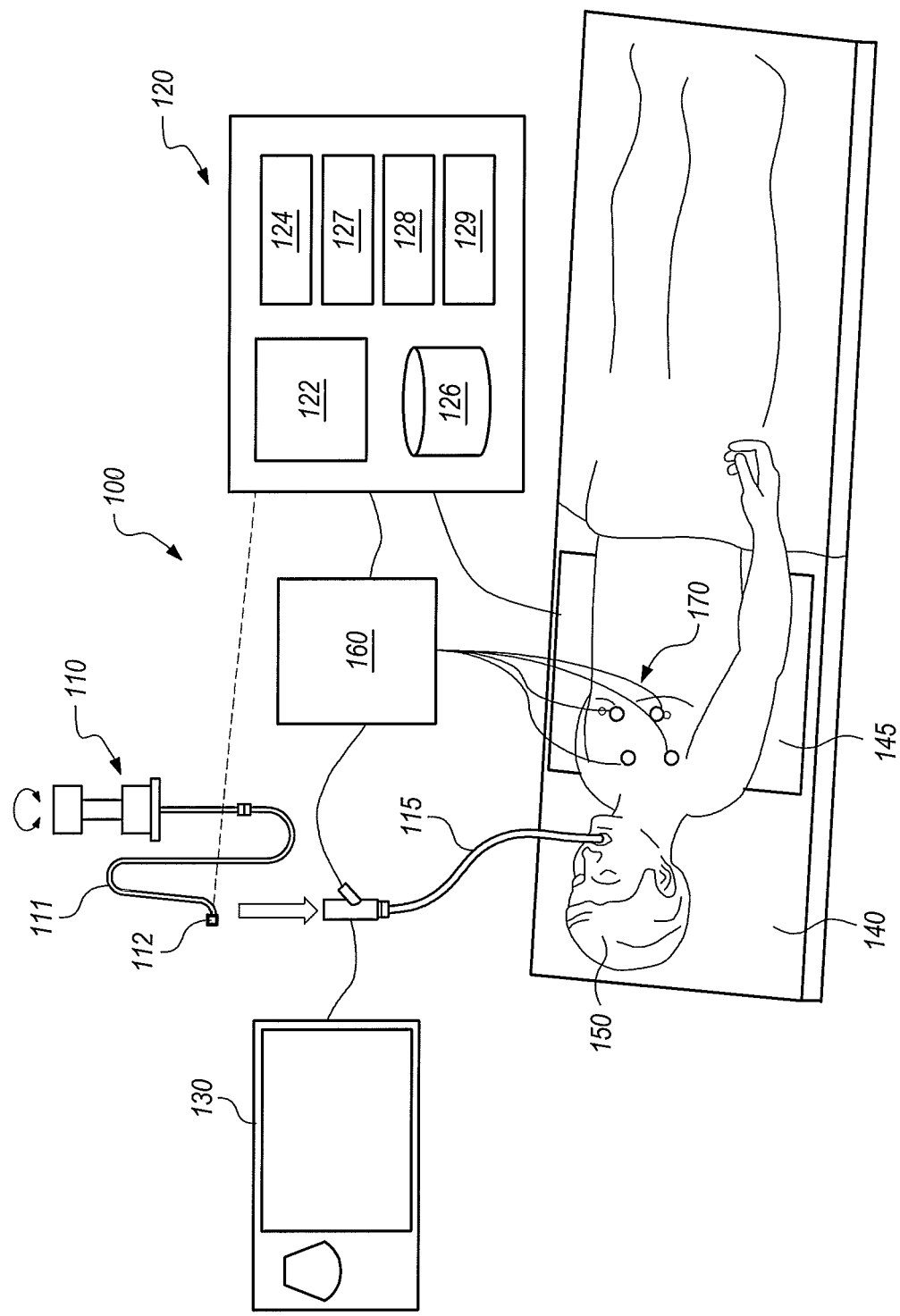
FIG. 1 shows an example electromagnetic navigation (EMN) system, in accordance with the present disclosure.

FIG. 1 illustrates an example electromagnetic navigation (EMN) system 100, which is configured to identify a location and/or an orientation of a medical device, or sensor thereof, navigating (e.g., to a target) within the patient's body by using an antenna assembly, which includes a plurality of antennas and generates EM fields. The EMN system 100 is further configured to augment CT, Mill, or fluoroscopic images in navigation through patient's body toward a target of interest, such as a deceased portion in a luminal network of a patient's lung.

The EMN system 100 includes a catheter guide assembly 110, a bronchoscope 115, a computing device 120, a monitoring device 130, an EM board 140, a tracking device 160, and reference sensors 170. The bronchoscope 115 is operatively coupled to the computing device 120 and the monitoring device 130 via a wired connection (as shown in FIG. 1) or wireless connection (not shown).

The bronchoscope 115 is inserted into the mouth of a patient 150 and captures images of the luminal network of the lung. In the EMN system 100, inserted into the bronchoscope 115 is a catheter guide assembly 110 for achieving access to the periphery of the luminal network of the lung of the patient 150. The catheter guide assembly 110 may include an extended working channel (EWC) 111 with an EM sensor 112 at the distal portion of the EWC 111. A locatable guide catheter (LG) may be inserted into the EWC 111 with another EM sensor at the distal portion of the LG. The EM sensor 112 at the distal portion of the EWC 111 or the LG is used to identify a location and/or an orientation of the EWC 111 or the LG while navigating through the luminal network of the lung. Due to the size restriction in the EWC 111 or the LG, in some embodiments, the EM sensor 112 may include only one single coil for detecting EM strength of an EM field over the patient 150. However, the number of coils in the EM sensor is not limited to one but may be two or more.

The computing device 120, such as, a laptop, desktop, tablet, or other similar computing device, includes a display 122, one or more processors 124, memory 126, an AC current driver 127 for providing AC current signals to the antenna assembly 145, a network card 128, and an input device 129. The particular configuration of the computing device 120 illustrated in FIG. 1 is provided as an example, but other configurations of the components shown in FIG. 1 as being included in the computing device 120 are also contemplated. In particular, in some embodiments, one or more of the components (122, 124, 126, 127, 128, and/or 129) shown in FIG. 1 as being included in the computing device 120 may instead be separate from the computing device 120 and may be coupled to the computing device 120 and/or to any other component(s) of the system 100 by way of one or more respective wired or wireless path(s) to facilitate the transmission of power and/or data signals throughout the system 100. For example, although not shown in FIG. 1, the AC current driver 127 may, in some example aspects, be separate from the computing device 120 and may be coupled to the antenna assembly 145 and/or coupled to one or more components of the computing device 120, such as the processor 124 and the memory 126, by way of one or more corresponding paths.

In some aspects, the EMN system 100 may also include multiple computing devices, wherein the multiple computing devices are employed for planning, treatment, visualization, or helping clinicians in a manner suitable for medical operations. The display 122 may be touch-sensitive and/or voice-activated, enabling the display 122 to serve as both input and output devices. The display 122 may display two dimensional (2D) images or three dimensional (3D) model of a lung to locate and identify a portion of the lung that displays symptoms of lung diseases.

The one or more processors 124 execute computer-executable instructions. The processors 124 may perform image-processing functions so that the 3D model of the lung can be displayed on the display 122 or location algorithm to identify a location and an orientation of the EM sensor 112. In embodiments, the computing device 120 may further include a separate graphic accelerator (not shown) that performs only the image-processing functions so that the one or more processors 124 may be available for other programs. The memory 126 stores data and programs. For example, data may be mapping data for the EMN or any other related data such as a HD map, image data, patients' medical records, prescriptions and/or history of the patient's diseases.

The HD map may include a plurality of gridpoints in a fine coordinate system of the EM volume in which a medical device (e.g., the EWC 111, LG, treatment probe, or other surgical devices) is to be navigated, and expected EM strengths at each of the plurality of gridpoints. When the EM sensor 112 senses EM strength at a point, the one or more processors 124 may compare the sensed EM strength with the expected EM strengths in the HD map and identify the location of the EM sensor 112 within the EM volume. Further, an orientation of the medical device may be also calculated based on the sensed EM strength and the expected EM strengths in the HD map.

As shown in FIG. 1, the EM board 140 is configured to provide a flat surface for the patient 150 to lie upon and includes an antenna assembly 145. When the patient 150 lies upon on the EM board 140, the antenna assembly 145 generates an EM field sufficient to surround a portion of the patient 150 or the EM volume. The antenna assembly 145 includes a plurality of antennas, each of which may include a plurality of loops. In one aspect, each antenna is configured to generate an EM waveform having a corresponding frequency. The number of antennas may be at least six. In an aspect, the number of antennas may be nine so that nine different EM waveforms can be generated.

In another aspect, a time multiplexing method is employed in generating the EM waveforms. For example, the antennas of the antenna assembly 145 may generate EM waveforms with the same frequency at different times during a period. In another aspect, frequency multiplexing method may be employed, where each antenna generates EM waveform having a frequency different from each other. In still another aspect, combination of the time multiplexing and frequency multiplexing methods may be employed. The antennas are grouped into more than one group. Antennas in the same group generate EM waveforms having the same frequency but at different times. Antennas in different groups may generate EM waveforms having different frequencies from each other. Corresponding de-multiplexing method is to be used to separate EM waveforms.

In an aspect, each antenna may have a geometric configuration (for instance, where the antennas each have geometric configurations based on linear portions of printed circuit board (PCB) traces or wires, which facilitate use of the superposition principle in computing the total contribution of the fields generated by way of each antenna to the total combined EM field within the volume) so that each portion of the plurality of loops can be expressed as mathematical relationship or equations, as described in further detail below. The magnetic field can thus be computed for each trace on the antenna and the contributions from all traces can be summed. Based on this geometric configuration, expected EM strength at each gridpoint in the HD map can be theoretically or mathematically calculated. Additional aspects of such example antennas and methods of manufacturing the antennas are disclosed in U.S. patent application Ser. No. 15/337,056, entitled "Electromagnetic Navigation Antenna Assembly and Electromagnetic Navigation System Including the Same," filed on Oct. 28, 2016, the entire contents of which are hereby incorporated by reference herein.

Figure 2:
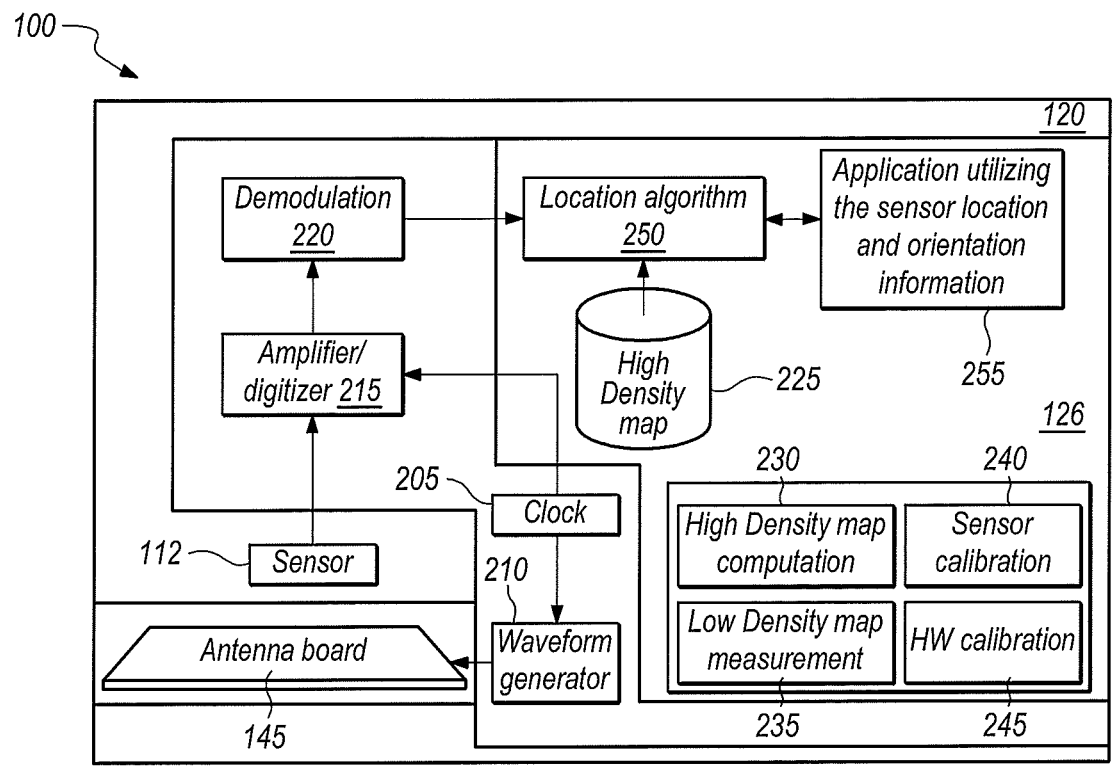
FIG. 2 is a block diagram of a portion of the EMN system of FIG. 1, in accordance with the present disclosure.

FIG. 2 shows a block diagram of a portion of the example electromagnetic navigation system 100 of FIG. 1, according to the present disclosure. In general, the computing device 120 of the EMN system 100 controls the antenna assembly 145 embedded in the EM board 140 to generate an EM field, receives sensed results from the EM sensor 112, and determines a location and an orientation of the EM sensor 112 in the EM volume.

The computing device 120 includes a clock 205, which generates a clock signal used for generating the EM field and sampling the sensed results. Since the same clock signal is used for generating the EM field and sampling the sensed EM field, synchronization between the magnetic field generation circuitry (e.g., a waveform generator 210) and the waveform acquisition circuitry (e.g., a digitizer 215) may be achieved. In other words, when the clock 205 provides a clock signal to the waveform generator 210 and the digitizer 215, the EM waveforms generated by the antenna assembly 145 are digitally sampled by digitizer 215 substantially at the same time. The digitizer 215 may include an analog-to-digital converter (ADC, which is not shown) to digitally sample the sensed results and an amplifier (which is not shown) to amplify the magnitude of the sensed result so that the magnitude of the sensed results is within the operable range of the ADC. In an aspect, the digitizer 215 may include a pre-amplifier and post-amplifier so that the magnitude of the sensed result is amplified to be within the operable range of the ADC by the pre-amplifier and digital samples are also amplified to the magnitude of the sensed result by the post-amplifier.

The demodulator 220 demodulates the digital samples to remove unwanted signals (e.g., noises) and to restore the EM waveforms, which have been generated by the antenna assembly 145. The demodulator 220 may use time de-multiplexing method, frequency de-multiplexing method, or combination of both to separate and identify the EM waveforms depending on the method used by the antennas of the antenna assembly 145 to generate the EM waveforms, and to determine EM strength affected by each of the antenna of the antenna assembly 145.

For example, when the antenna assembly 145 includes six antennas, the demodulator 220 is capable of identifying six EM strengths, which is sensed by the EM sensor 112, for the six antennas, respectively. In a case when the number of antennas is nine, the outputs of the demodulator 220 may be expressed in a form of a nine by one matrix. Based on the modulation method (e.g., time multiplexing, frequency multiplexing, or a combination thereof) utilized by the antennas, the demodulator 220 demodulates the sensed result.

For example, when the antennas of the antenna assembly 145 utilize frequency multiplexing, the demodulator 220 may use a set of finely tuned digital filters. Orthogonal frequency division multiplexing may also be utilized, in which the EM field and sampling frequencies are chosen in such a way that only the desired frequency from a specific antenna is allowed to pass while other frequencies are precisely stopped. In an aspect, the demodulator 220 may use a multiple tap orthogonal frequency matched filter, in which the digital filter for a specific frequency is tuned to the desired demodulation window.

The memory 126 may store data and programs related to identification of a location and an orientation. The data includes a high density (HD) map 225, which includes a plurality of gridpoints according to the fine coordinate system for the EM volume and expected EM strengths at the gridpoints. The HD map 225 may be based on three-axis coordinate system, where each gridpoint has three coordinates corresponding to the three axes, respectively. In this case, the expected EM strength at each gridpoint may include one EM strength value along each axis for each EM waveform. For example, if there are nine antennas generating nine different EM waveforms, each of which having a separate frequency, and three axes are x, y, and z axes, the expected EM strength may include nine EM strength values along the x axis, nine EM strength values along the y axis, and nine EM strength values along the z axis, at each gridpoint. Such expected EM strength at each gridpoint may be expressed in a nine by three matrix form.

The HD map 225 may be made with computations 230, which includes theoretically calculated EM strengths at each axis at each gridpoint in the fine coordinate system, and measurement 235, which includes measurements at each axis at each gridpoint in the coarse coordinate system. The fine coordinate system includes all the gridpoints in the coarse coordinate system and the gridpoints of the fine coordinate system are more finely distributed than those of the coarse coordinate system. By using the geometric configuration of the antennas of the antenna assembly 145, measurement may not have to be made with the fine coordinate system. Rather, the measurement may be made in the coarse coordinate system and theoretical computations may be made in the fine coordinate system. By combining the measurements 235 in the coarse coordinate system with the theoretical computations 230 in the fine coordinate system, the HD map 225 may be generated. Generation of the HD map 225 based on the measurement 235 and calculations 230 will be described in further detail with respect to FIG. 4 below.

After passage of time or due to foreign objects near the EMN system 100, measurements by the EM sensor 112 or other hardware may need to be calibrated. Such calibration data may be also stored in the memory 126 in a form of sensor calibration 240 and hardware calibration 245.

When the computing device 120 receives measurement data from the EM sensor 112 via the demodulator 220, the computing device 120 uses the location algorithm 250, which is also stored in the memory 126, with the HD map 225 to identify the location and the orientation of the EM sensor 112 in the fine coordinate system. Identification of the location and/or the orientation will be described in further detail with respect to FIG. 5 below.

The location algorithm 250 may utilize any error minimization algorithm in identifying the location and the orientation of the EM sensor 112. For example, Levenberg-Marquardt algorithm may be employed to minimize errors between the expected EM strengths of the HD density map and the sensed results. Other error minimization methods or algorithms, which a person having ordinary skill in the art can readily appreciate, may also be utilized without departing from the scope of this disclosure.

The memory 126 further includes applications 255, which can be utilized by the computing device 120 of the EMN system 100 and which uses information regarding the location and the orientation of the EM sensor 112. Such application 255 may be a displaying application, which displays a graphical representation of a medical device, on which the EM sensor 112 is mounted or installed, at the location of the EM sensor 112 and along the orientation of the EM sensor 112 in the EM volume, an application for treatment, which determines whether a medical device is near a target of interest, or any other applications, which use the location and the orientation of the EM sensor 112.

Figure 3:
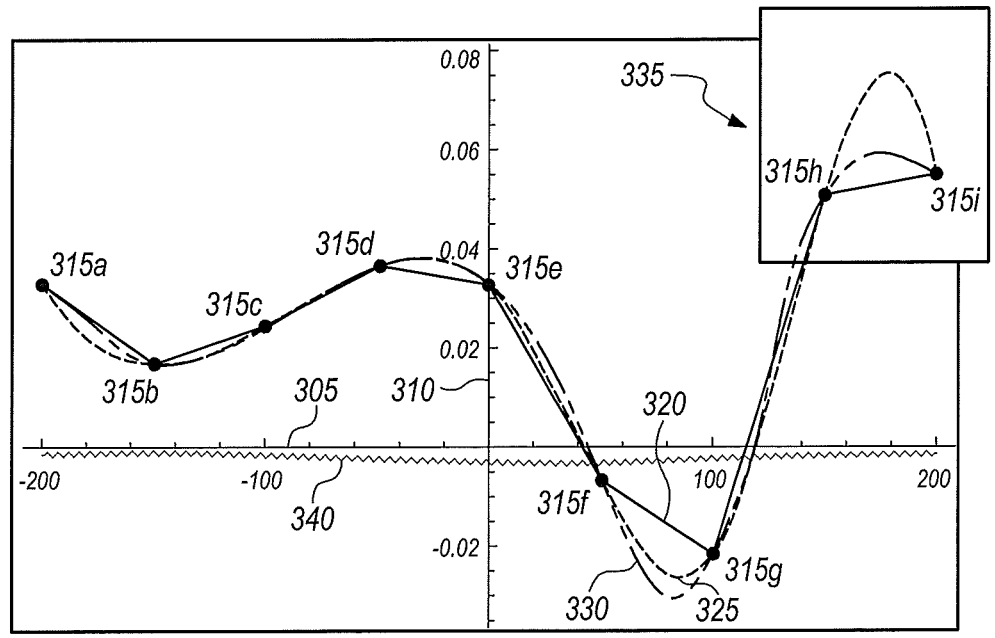
FIG. 3 is a graphical illustration of example low density measurements and related curves, in accordance with the present disclosure.

FIG. 3 is a graphical illustration of multiple curves 320, 325, 330, and 340, as well as discrete EM field strength measurements 315a-315i taken in the coarse coordinate system. The horizontal axis may represent any axis among x, y, and z axes for the EM volume and the vertical axis represents a magnitude of EM field strengths. Gridpoints of the coarse coordinate system are shown separated by 50 millimeters and measured EM strengths at the gridpoints of the coarse coordinate system are shown as black dots 315a-315i.

In some aspects, measurements may be taken at a specific hospital rooms and beds, where the EMN system 100 will be used, by way of a measurement jig, which includes three coils sensing an EM field strength in each of three different directions (e.g., x, y, and z axes). Examples of such a measurement jig are disclosed by Provisional U.S. Patent Application No. 62/237,084, entitled "Systems And Methods For Automated Mapping And Accuracy-Testing," filed on Oct. 5, 2015, the entire contents of which are hereby incorporated herein by reference.

Based on the measurement values at LD gridpoints 315a-315i, interpolation may be used to generate first and second interpolated curves, 320 and 325. In one example, the first interpolated curve 320 is generated by a linear interpolation method and the second interpolated curve 325 is generated by B-spline interpolation. Calculated EM strengths at gridpoints in the HD map are also interpolated to generate a third interpolated curve 330.

As shown in box 335, the first, second, and third interpolated curves 320, 325, 330 are substantially different from each other between two gridpoints 315h and 315i. The first interpolated curve 320 is lower than the third interpolated curve 330, and the second interpolated curve 325 is much higher than the second and third interpolated curves 325 and 330. Due to these big differences, an error may be apparent if only one of the three interpolated curves is used.

In order to minimize such differences, a fourth interpolated curve 340 is used. The fourth curve 340 is generated by calculating discrepancies between theoretical calculations and measurements at the LD gridpoints, such as 315a-315i, and interpolating the discrepancies for the HD gridpoints. By adding the fourth interpolated curve 340 to the third interpolated curve 330 at the HD gridpoints, expected EM strength at each gridpoints in the HD map is obtained and higher accuracy may be obtained. Detailed descriptions regarding how to generate the HD map is described with respect to FIG. 4 below.

Figure 4:
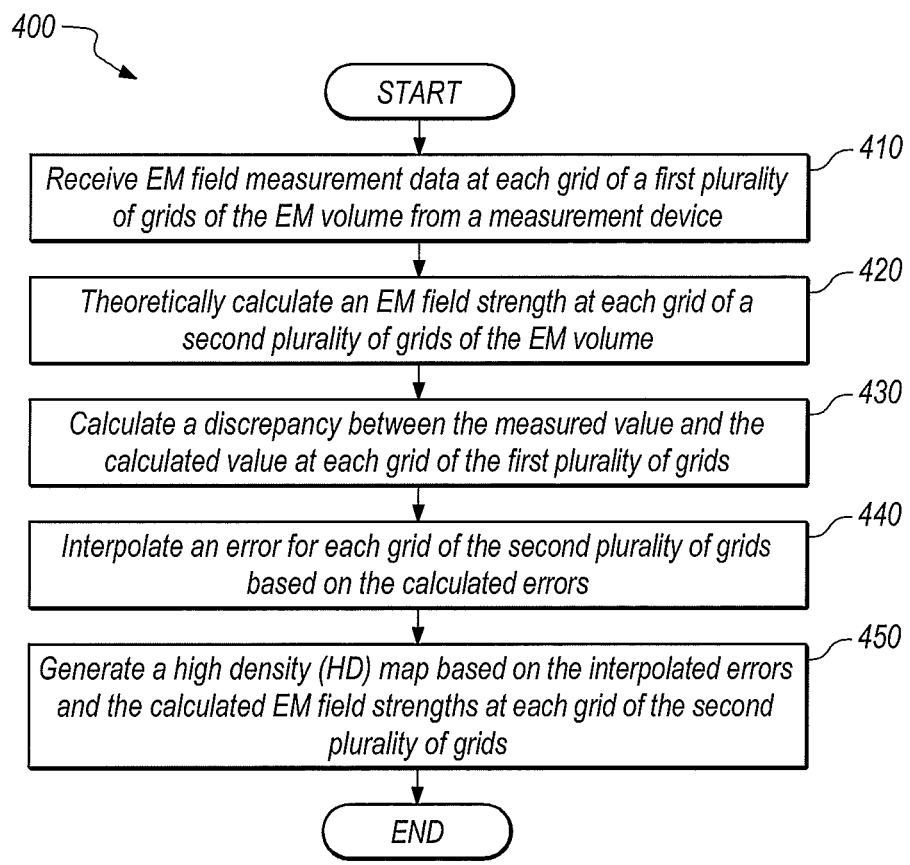
FIG. 4 is a flowchart illustrating an example method for generating a high density map, in accordance with the present disclosure.

FIG. 4 is a flowchart illustrating an example method 400 for generating an HD map based on theoretical calculations in the fine coordinate system and measurements in the coarse coordinate system. Measurements may be performed for the EM field generated by the antennas of the antenna assembly 145 of FIG. 1, each of which having a corresponding geometric configuration. At 410, EM field measurements at all gridpoints in the coarse coordinate system are received from a measurement jig. The measurements may include three different measurements along three axes in the coarse coordinate system for each EM waveform. Thus, when there are nine antennas, the measurements at one gridpoint may include three values for the three different axes and nine of three values for the nine different waveforms, respectively. In an aspect, these measurements may be in a form of nine by three matrix.

At 420, based on the geometric configuration of each antenna of the antenna assembly 145, EM field strength is theoretically or mathematically calculated. As described above, each antenna includes a plurality of loops, which have geometric configurations. In other words, each loop of the antenna can be expressed in a form of mathematical equations or is made of simply linear portions. Thus, EM strength at any gridpoints in the fine coordinate system may be calculated by using Biot-Savart-Laplace law as follows:

$$B(r) = \frac{\mu_0}{4\pi} \int_C \frac{Idl \times r'}{|r'|^3}, \tag{1}$$

where B(r) is the EM strength at the gridpoint r influenced by the linear portion C, to is a magnetic constant of the vacuum permeability, $4\eta \times 10$-7 V·s/(A·m), $\int_C$ is a symbol of line integral on the linear portion C, I is the magnitude of the current passing through the linear portion C, dl is a vector whose magnitude is the length of the differential element of the linear portion C in the direction of current, r' is a displacement vector from the differential element dl of the linear portion C to the gridpoint r, and x is a vector symbol representing a cross product between two vectors. Since the linear portion C is a simple line and each loop of the antenna includes multiple linear portions, total EM strength at the gridpoint r can be a sum of the EM strengths influenced by all the linear portions of the antenna. Further, the EM strength at the gridpoint r by the plural antennas is calculated in the same way. In other words, the total EM strength at gridpoint r may include three calculated values for the three different axes (e.g., x, y, and z axes) for one antenna, and nine of three calculated values for the nine antennas, in a case when there are nine antennas. In an aspect, the calculated EM strength may be expressed in a nine by three matrix form.

At 430, a discrepancy is calculated between the measured EM field and the calculated EM field at each gridpoint in the coarse coordinate system. In an aspect, the discrepancy may be made smaller by calibrating parameters of the three coil sensor of the measurement jig, calibrating the antennas, or calibrating parameters (e.g., frequencies or phases for the waveform generator 210) of the computing device of the EMN system.

At 440, the calculated discrepancies at gridpoints in the coarse coordinate system are interpolated for gridpoints in the fine coordinate system. Any method of interpolation including linear interpolation, b-spline interpolation, etc. may be used.

At 450, the interpolated discrepancies are added to the theoretical calculations of the EM field to from expected EM field strength at each gridpoint in the fine coordinate system. The expected EM field strength at each gridpoint may be in a form of a nine by three matrix in a case when there are nine separate EM waveforms. The HD map may further include a pseudo-inverse of the expected EM field strength at each gridpoint in the HD map. This pseudo-inverse may be used in identifying a location and an orientation of the EM sensor, which is described in further detail with respect to FIG. 5 below.

Figure 5:
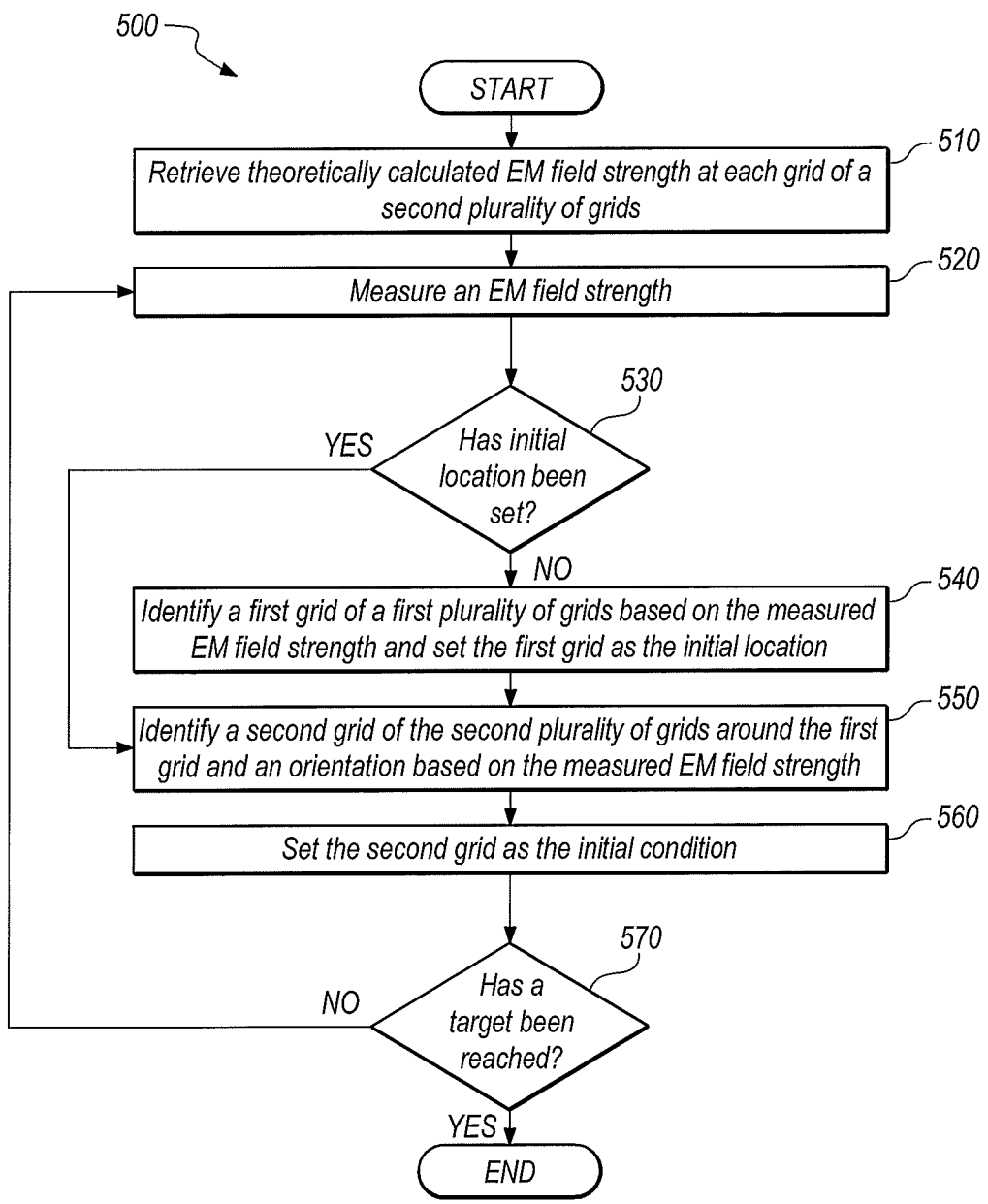
FIG. 5 is a flowchart illustrating an example method for identifying a location and/or an orientation of a sensor, in accordance with the present disclosure.

FIG. 5 is a flowchart illustrating an example method 500 for identifying a location and/or an orientation of an EM sensor, for example, mounted on a medical device, which is navigated within a patient's body, in accordance with the present disclosure. The method 500 may be used while a medical device navigates inside the patient's body. At 510, the HD map, which includes expected EM field strength at each gridpoint of the HD map, is retrieved from a memory.

As described above, the expected EM field strengths are based on the theoretical computations in the fine coordinate system and measurements in the coarse coordinate system.

The EM sensor mounted on the medical device periodically transmits sensed EM field strength to an EMN computing device, which digitally samples the sensed EM field strength. The EMN computing device measures the EM field strength based on the digital samples in step 520.

At 530, it is determined whether an initial location is set as an initial condition. If it is determined that the initial location is not set, the EMN computing device compares all gridpoints in the coarse coordinate system with the measured EM field strength, simply pickups, to find an approximate gridpoint in the coarse coordinate system near the location of the EM sensor, as an initial location, at 540.

In an embodiment, a following error function may be used at 540:

$$E = \sum_{\alpha=1}^{N} \left(\vec{B_\alpha}(a,b,c) \cdot \vec{n}(a,b,c) - V_\alpha\right)^2 + b\left(|\vec{n}|^2 - g^2\right)^2, \quad (2)$$

where E is the error value, $\alpha$ is a counter, N is the number of antennas, (a,b,c) is a gridpoint in the coarse coordinate system, $\vec{B_\alpha}(a,b,c)$ is a vector, one by three matrix, including an expected EM field strength at (a,b,c) influenced by the $\alpha$-th antenna, "·" is a symbol of dot product between two vectors, $\vec{n}(a,b,c)$ is an orientation of the EM sensor, and $V_\alpha$ is a vector, one by one matrix, including a pickup influenced by the $\alpha$-th antenna, b is a parameter to control a gain weight, and g is a gain of the EM sensor. In an aspect, the parameter b is used when the gain of the EM sensor is known and fixed. The value for the parameter b may be chosen so as not to dominate the error function E. In another aspect, when the gain of the EM sensor is not known, the parameter b may be set to zero or the gain squared, $g^2$, is assumed to be equal to the squared norm of the orientation vector n.

In some examples, for convenience, the parameter b is assumed to be zero. In this case, the error function E becomes:

$$\sum_{\alpha=1}^{N} \left(\vec{B_\alpha}(a,b,c) \cdot \vec{n}(a,b,c) - V_\alpha\right)^2. \quad (3)$$

This error function is useful in identifying a location in the coarse or fine coordinate system. In an aspect, the error function is not limited to the above equation (2) or (3) and can be any error function that a person of ordinary skill in the art would readily appreciate without departing from the scope of this disclosure. For example, the error function E may be:

$$|\vec{B}(a,b,c) - V|_1 \text{ or } |\vec{B}(a,b,c) - V|_2,$$

where $\|\cdot\|_1$ or $\|\cdot\|_2$ represents an L1 or L2 norm of the vector inside of the symbol, respectively.

Figure 6:
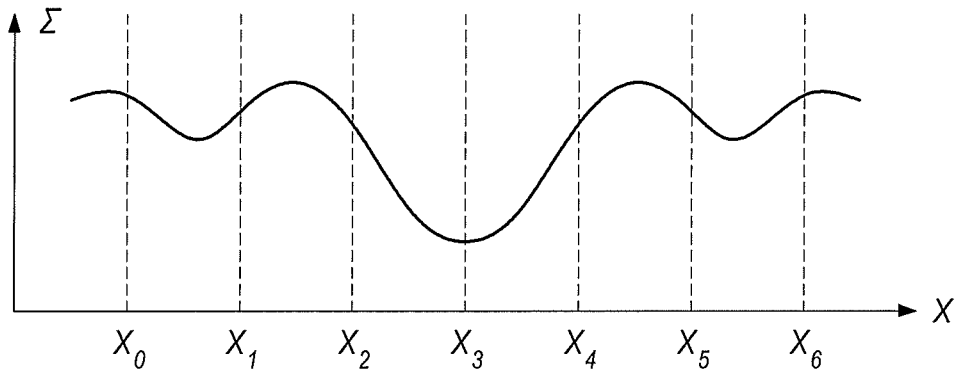
FIG. 6 is a graphical illustration of an example error function, having multiple local minima, of a discrepancy between a measurement value and a calculated value, in accordance with the present disclosure.

Referring briefly to FIG. 6, a curve of an error function along one axis is shown to illustrate how selection of an initial location may impact the determination of a location that provides the global minimum of the error. The horizontal axis represents a location along one axis (e.g., x, y, or z axis) and the vertical axis represents a magnitude of the error function. If the initial location is set to be near $X_0$ or $X_1$, the location giving a local minimum will be between $X_0$ and $X_1$. If the initial location is set to be $X_5$ or $X_6$, the location giving a local minimum will be between $X_5$ and $X_6$. In contrast, if the initial location is set to be one of $X_2$, $X_3$, or $X_4$, the location giving a local minimum will be between $X_3$ and $X_4$, which gives the accurate global minimum. Thus, referring back to FIG. 5, in a case when there is no set initial location, the method 500 evaluates the error function at every gridpoint in the coarse coordinate system to find a first gridpoint, which provides the global minimum, in step 540.

The error function E includes a term, the orientation vector $\vec{n}$, which, at 540, may also be identified as follows:

$$\vec{n}(a,b,c) = \vec{B}(a,b,c)^{-1} \cdot V \quad (4),$$

where $\vec{B}(a,b,c)^{-1}$ is a pseudo-inverse of $\vec{B}(a,b,c)$, and V includes pickups. In one example, if the total number of antennas in the antenna assembly is nine, $\vec{B}(a,b,c)$ is a nine by three matrix, $\vec{B}(a,b,c)^{-1}$ is a three by nine matrix, and V is a nine by one matrix. Thus, $\vec{B}(a,b,c)^{-1} \cdot V$ results in a three by one matrix, which is a column vector representing an orientation matrix, $\vec{n}(a,b,c)$ at gridpoint (a,b,c) in the coarse coordinate system.

Based on equation (3), the error function is evaluated. Errors of all gridpoints in the coarse coordinate system are compared with each other, and the gridpoint that provides the smallest error is selected as a first gridpoint and is set as the initial location at 540. After the initial location is set at 540, 550 follows. Also, at 530, when it is determined that the initial location is set, the step 550 is performed.

At 550, a predetermined number of gridpoints around the initial location are selected to calculate the error function in the same way as in equation (2) or (3). For example, if the predetermined number of gridpoints is three, three gridpoints from the initial location in both directions along x, y, and z axes form a cube, 7 by 7 by 7 gridpoints. Thus, 343 gridpoints are selected to calculate the error function, and one among the selected gridpoints, which provides the smallest error, is selected as a second gridpoint, i.e., the location of the EM sensor. The corresponding orientation vector is also set as the orientation of the EM sensor in step 550. The second gridpoint is set as the initial location in step 560.

According to one aspect, in step 540, the error may be compared with a predetermined threshold. If the error is less than the predetermined threshold, that gridpoint is selected as the second gridpoint or the location of the EM sensor and corresponding orientation vector is selected as the orientation of the EM sensor.

In step 570, it is determined whether the target has been reached. When it is determined that the target has not been reached, steps 520-570 are repeated until the target is reached. Otherwise, the method 500 ends.

Figure 7:
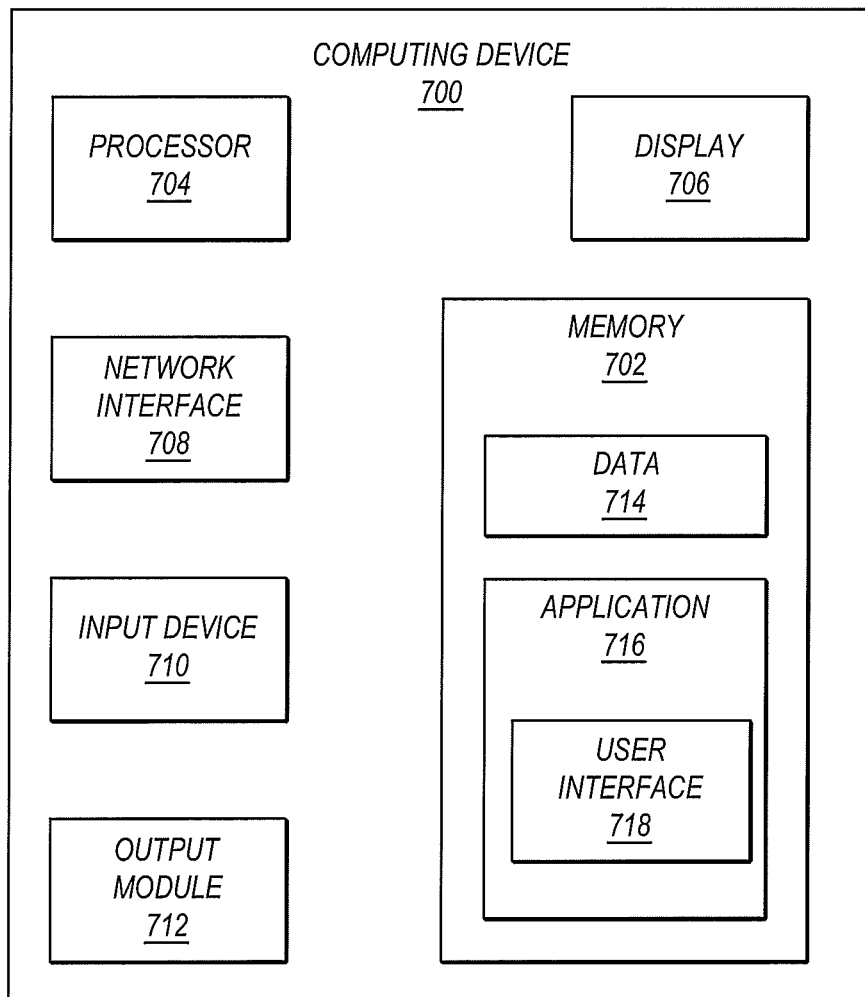
FIG. 7 is a block diagram of a computing device for use in various embodiments of the present disclosure.

Turning now to FIG. 7, there is shown a block diagram of a computing device 700, which can be used as the computing device 120 of the EMN system 100, the tracking device 160, or a computer performing the method 400 of FIG. 4 or the method 500 of FIG. 5. The computing device 700 may include a memory 702, a processor 704, a display 706, network interface 708, an input device 710, and/or output module 712.

The memory 702 includes any non-transitory computer-readable storage media for storing data and/or software that is executable by the processor 704 and which controls the operation of the computing device 700. In an embodiment, the memory 702 may include one or more solid-state storage devices such as flash memory chips. Alternatively or in addition to the one or more solid-state storage devices, the memory 702 may include one or more mass storage devices connected to the processor 704 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 704. That is, computer readable storage media include non-transitory, volatile and non-volatile, removable and non-removable media implemented in any method or technology for storage of information such as computer-readable instructions, data structures, program modules or other data. For example, computer-readable storage media include RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the computing device 700.

The memory 702 may store application 716 and data 714. The application 716 may, when executed by the processor 704, cause the display 706 to present user interface 718 on its screen.

The processor 704 may be a general purpose processor, a specialized graphic processing unit (GPU) configured to perform specific graphics processing tasks while freeing up the general purpose processor to perform other tasks, and/or any number or combination of such processors.

The display 706 may be touch-sensitive and/or voice-activated, enabling the display 706 to serve as both an input and output device. Alternatively, a keyboard (not shown), mouse (not shown), or other data input devices may be employed.

The network interface 708 may be configured to connect to a network such as a local area network (LAN) consisting of a wired network and/or a wireless network, a wide area network (WAN), a wireless mobile network, a Bluetooth network, and/or the internet. For example, the computing device 700 may receive measurement data and variables, and perform the method 400 of FIG. 4 to generate a HD map. The computing device 700 may receive updates to its software, for example, application 716, via network interface 708. The computing device 700 may also display notifications on the display 706 that a software update is available.

In another aspect, the computing device 700 may receive computed tomographic (CT) image data of a patient from a server, for example, a hospital server, internet server, or other similar servers, for use during surgical ablation planning. Patient CT image data may also be provided to the computing device 700 via a removable memory.

Input device 710 may be any device by means of which a user may interact with the computing device 700, such as, for example, a mouse, keyboard, foot pedal, touch screen, and/or voice interface.

Output module 712 may include any connectivity port or bus, such as, for example, parallel ports, serial ports, universal serial busses (USB), or any other similar connectivity port known to those skilled in the art.

The application 716 may be one or more software programs stored in the memory 702 and executed by the processor 704 of the computing device 700. During generation of the HD map, one or more software programs in the application 716 may be loaded from the memory 702 and executed by the processor 704 to generate the HD map. In an embodiment, during a navigation phase, one or more programs in the application 716 may be loaded, identify the location and the orientation of an EM sensor mounted on a medical device, and display the medical device at the location along the orientation on a screen overlaid with other imaging data, such as CT data or a three dimensional model of a patient. In another embodiment, during a treatment phase, one or more programs in the application 716 may guide a clinician through a series of steps to identify a target, size the target, size a treatment zone, and/or determine an access route to the target for later use during the procedure phase. In some other embodiments, one or more programs in the application 716 may be loaded on computing devices in an operating room or other facility where surgical procedures are performed, and is used as a plan or map to guide a clinician performing a surgical procedure by using the information regarding the location and the orientation.

The application 716 may be installed directly on the computing device 700, or may be installed on another computer, for example a central server, and opened on the computing device 700 via the network interface 708. The application 716 may run natively on the computing device 700, as a web-based application, or any other format known to those skilled in the art. In some embodiments, the application 716 will be a single software program having all of the features and functionality described in the present disclosure. In other embodiments, the application 716 may be two or more distinct software programs providing various parts of these features and functionality. For example, the application 716 may include one software program for generating a HD map, another one for identifying a location and an orientation, and a third program for navigation and treatment program. In such instances, the various software programs forming part of the application 716 may be enabled to communicate with each other and/or import and export various data including settings and parameters.

The application 716 may communicate with a user interface 718 which generates a user interface for presenting visual interactive features to a user, for example, on the display 706 and for receiving input, for example, via a user input device. For example, user interface 718 may generate a graphical user interface (GUI) and output the GUI to the display 706 for viewing by a user.

In a case that the computing device 700 may be used as the EMN system 100, the control workstation 102, or the tracking device 160, the computing device 700 may be linked to the display 130, thus enabling the computing device 700 to control the output on the display 130 along with the output on the display 706. The computing device 700 may control the display 130 to display output which is the same as or similar to the output displayed on the display 706. For example, the output on the display 706 may be mirrored on the display 130. Alternatively, the computing device 700 may control the display 130 to display different output from that displayed on the display 706. For example, the display 130 may be controlled to display guidance images and information during the surgical procedure, while the display 706 is controlled to display other output, such as configuration or status information of an electrosurgical generator 101 as shown in FIG. 1.

The application 716 may include one software program for use during the planning phase, and a second software program for use during the treatment phase. In such instances, the various software programs forming part of application 716 may be enabled to communicate with each other and/or import and export various settings and parameters relating to the navigation and treatment and/or the patient to share information. For example, a treatment plan and any of its components generated by one software program during the planning phase may be stored and exported to be used by a second software program during the procedure phase.

Although embodiments have been described in detail with reference to the accompanying drawings for the purpose of illustration and description, it is to be understood that the inventive processes and apparatus are not to be construed as limited. It will be apparent to those of ordinary skill in the art that various modifications to the foregoing embodiments may be made without departing from the scope of the disclosure. For example, various steps of the methods described herein may be implemented concurrently and/or in an order different from the example order(s) described herein.

What is claimed is:

1. A surgical navigation system, the system comprising:
an antenna assembly configured to radiate an electromagnetic (EM) field;
an EM sensor configured to be navigated within the EM field and to measure an EM field strength;
a processor; and
a memory storing a calculated theoretical EM field strength at each gridpoint of a first plurality of gridpoints of the EM field, wherein the calculated theoretical EM field strength at each gridpoint of the first plurality of gridpoints of the EM field is based on a sum of theoretical EM field strength calculations from a plurality of linear portions of an antenna of the antenna assembly, the memory storing processor-executable instructions that, when executed by the processor, cause the processor to:
retrieve from the memory the calculated theoretical EM field strength at each gridpoint of the first plurality of gridpoints;
identify a first gridpoint among a second plurality of gridpoints of the EM field based on the measured EM field strength and a high density (HD) map; and
identify a location of the EM sensor based on the HD map using the first gridpoint among the second plurality of gridpoints as an initial condition.

2. The system according to claim 1, wherein the antenna assembly includes at least six antennas, each of the antennas including a plurality of loops.

3. The system according to claim 2, wherein the plurality of loops has a geometric configuration.

4. The system according to claim 1, wherein the HD map includes the calculated theoretical EM field strength at each gridpoint of the first plurality of gridpoints in the EM field.

5. The system according to claim 4, wherein the HD map further includes a pseudo-inverse of the calculated theoretical EM field strength at each gridpoint of the first plurality of gridpoints.

6. The system according to claim 1, wherein the identifying the first gridpoint includes:
identifying an orientation vector $\vec{n}_{(a,b,c)}$, where (a,b,c) is a gridpoint in the first plurality of gridpoints, satisfying the following condition:
$\vec{n}_{(a,b,c)} \approx \vec{B}_{(a,b,c)}^{-1} \cdot V$, where $\vec{B}_{(d,e,f)}^{-1}$ is a pseudo-inverse of $\vec{B}_{(a,b,c)}^{-1}$, which is a calculated EM field strength at gridpoint (a,b,c) in the HD map;
calculating a difference between $\vec{B}_{(a,b,c)} \cdot \vec{n}_{(a,b,c)}$ and V; and
selecting, as the first gridpoint, a gridpoint (A,B,C) of the first plurality of gridpoints where a difference between $\vec{B}_{(A,B,C)} \cdot \vec{n}$ and V is the smallest.

7. The system according to claim 1, wherein the identifying the location includes:
identifying an orientation vector $\vec{n}_{(d,e,f)}$, where (d,e,f) is a gridpoint in the second plurality of gridpoints and is located within a predetermined distance from the first gridpoint (A,B,C), satisfying the following condition:
$\vec{n}_{(d,e,f)} \approx \vec{B}_{(d,e,f)}^{-1} \cdot V$, where $\vec{B}_{(d,e,f)}^{-1}$ is a pseudo-inverse of $\vec{B}_{(d,e,f)}$, which is a calculated EM field strength at gridpoint (d,e,f) in the HD map;
calculating a difference between $\vec{B}_{(d,e,f)} \cdot \vec{n}_{(d,e,f)}$ and V; and
selecting a second gridpoint (D,E,F) from among the second plurality of gridpoints, where a difference between $\vec{B}_{(D,E,F)} \cdot \vec{n}_{(D,E,F)}$ and V is the smallest.

8. The system according to claim 7, wherein $\vec{n}_{(D,E,F)}$ is related to the orientation of the EM sensor.

9. The system according to claim 7, wherein the second gridpoint (D,E,F) is the location of the EM sensor.

10. The system according to claim 1, wherein the first plurality of gridpoints includes the second plurality of gridpoints and at least one additional gridpoint not included in the second plurality of gridpoints.

11. A surgical navigation system, the system comprising:
an antenna assembly configured to radiate an electromagnetic (EM) field within an EM volume;
an EM sensor configured to be navigated within the EM volume and to measure an EM field strength based on the EM field;
a processor; and
a memory storing a calculated theoretical EM field strength at each gridpoint of a first plurality of gridpoints of the EM volume, wherein the calculated theoretical EM field strength at each gridpoint of the first plurality of gridpoints of the EM volume is based on a sum of theoretical EM field strength calculations from a plurality of linear portions of the antenna assembly, the memory storing processor-executable instructions that, when executed by the processor, cause the processor to:
retrieve from the memory the calculated theoretical EM field strength of each of the first plurality of gridpoints;
identify a first gridpoint among a second plurality of gridpoints of the EM volume based on the measured EM field strength and a high density (HD) map; and
identify, using the first gridpoint, a location of the EM sensor based on the HD map.

12. The system according to claim 11, wherein the position of the EM sensor is identified using the first gridpoint as an initial condition.

13. The system according to claim 11, wherein the calculated theoretical EM field strength at each gridpoint of the first plurality of gridpoints of the EM volume is based on the sum of theoretical EM field strength calculations from the plurality of linear portions of an antenna of the antenna assembly.

14. The system according to claim 11, wherein the first plurality of gridpoints includes the second plurality of gridpoints and at least one additional gridpoint not included in the second plurality of gridpoints.

15. The system according to claim 11, wherein the HD map includes the calculated theoretical EM field strength at each gridpoint of the first plurality of gridpoints in the EM volume.

16. The system according to claim 15, wherein the HD map further includes a pseudo-inverse of the calculated theoretical EM field strength at each gridpoint of the first plurality of gridpoints.

17. A surgical navigation system, the system comprising:
- an electromagnetic (EM) sensor configured to be navigated within an EM field and to measure an EM field strength;
- a processor; and
- a memory storing a calculated theoretical EM field strength at each gridpoint of a first plurality of gridpoints of the EM field, wherein the calculated theoretical EM field strength at each gridpoint of the first plurality of gridpoints of the EM field is based on a sum of theoretical EM field strength calculations from a plurality of linear portions of an antenna assembly, the memory storing processor-executable instructions that, when executed by the processor, cause the processor to:
  - retrieve from the memory the calculated theoretical EM field strength of each of the first plurality of gridpoints;
  - identify a first gridpoint among a second plurality of gridpoints of the EM field based on an EM field strength measured by the EM sensor and a high density (HD) map; and
  - identify, using the first gridpoint, a location of the EM sensor based on the HD map.

18. The system according to claim 17, wherein the position of the EM sensor is identified using the first gridpoint as an initial condition.

19. The system according to claim 17, wherein the calculated theoretical EM field strength at each gridpoint of the first plurality of gridpoints of the EM field is based on the sum of theoretical EM field strength calculations from the plurality of linear portions of an antenna of the antenna assembly.

20. The system according to claim 17, wherein the first plurality of gridpoints includes the second plurality of gridpoints and at least one additional gridpoint not included in the second plurality of gridpoints.

* * * * *